(12) United States Patent
Terai

(10) Patent No.: US 9,147,843 B2
(45) Date of Patent: Sep. 29, 2015

(54) ORGANIC SEMICONDUCTOR MATERIAL

(71) Applicant: SUMITOMO CHEMICAL COMPANY, LIMITED, Chuo-ku, Tokyo (JP)

(72) Inventor: Hiroki Terai, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/391,041

(22) PCT Filed: Apr. 16, 2013

(86) PCT No.: PCT/JP2013/061701
§ 371 (c)(1),
(2) Date: Oct. 7, 2014

(87) PCT Pub. No.: WO2013/161728
PCT Pub. Date: Oct. 31, 2013

(65) Prior Publication Data
US 2015/0065671 A1    Mar. 5, 2015

(30) Foreign Application Priority Data

Apr. 25, 2012    (JP) .................. 2012-099605

(51) Int. Cl.
*C08G 75/00*    (2006.01)
*H01L 51/00*    (2006.01)
(Continued)

(52) U.S. Cl.
CPC .......... *H01L 51/0036* (2013.01); *C07D 495/06* (2013.01); *C08G 61/123* (2013.01);
(Continued)

(58) Field of Classification Search
CPC .................. C08G 2261/3246; C08G 2261/344; C08G 2261/354; C08G 2261/3243; H01L 51/0541; H01L 51/0545; H01L 51/0043
USPC .................. 528/377, 378, 370, 380
See application file for complete search history.

(56) References Cited

U.S. PATENT DOCUMENTS 6,049,428 A    4/2000 Khan et al.
2012/0205596 A1    8/2012 Yoshimura et al.

FOREIGN PATENT DOCUMENTS

JP    2009-009964 A    1/2009
JP    2009-033067 A    2/2009
(Continued)

OTHER PUBLICATIONS

International Search Report for PCT/JP2013/061701 dated Jul. 16, 2013 [PCT/ISA/210].    (Continued)

*Primary Examiner* — Shane Fang
(74) *Attorney, Agent, or Firm* — Sughrue Mion, PLLC

(57) ABSTRACT

A compound represented by the formula (1). A polymer compound comprising the compound. An organic semiconductor material comprising the compound or the polymer compound. An organic semiconductor device comprising an organic layer comprising the organic semiconductor material. An organic transistor comprising a source electrode, a drain electrode, a gate electrode and an active layer, wherein the active layer comprises the organic semiconductor material.

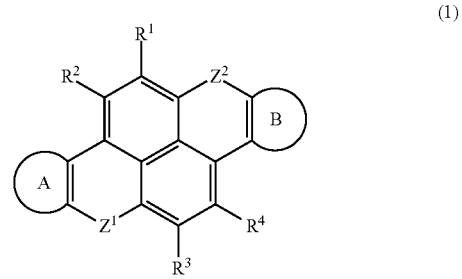

(1)

5 Claims, 3 Drawing Sheets

(51) Int. Cl.
*C07D 495/06* (2006.01)
*C08G 61/12* (2006.01)
*H01L 51/42* (2006.01)
*H01L 51/05* (2006.01)

(52) U.S. Cl.
CPC .......... *C08G61/126* (2013.01); *H01L 51/0074* (2013.01); *H01L 51/0545* (2013.01); *C08G 2261/148* (2013.01); *C08G 2261/1412* (2013.01); *C08G 2261/3223* (2013.01); *C08G 2261/3246* (2013.01); *C08G 2261/344* (2013.01); *C08G 2261/354* (2013.01); *C08G 2261/411* (2013.01); *C08G 2261/92* (2013.01); *H01L 51/0043* (2013.01); *H01L 51/0504* (2013.01); *H01L 51/0541* (2013.01); *H01L 51/42* (2013.01)

(56) References Cited

FOREIGN PATENT DOCUMENTS

| JP | 2009-182033 A | 8/2009 |
|----|---------------|--------|
| JP | 2009-302472 A | 12/2009 |
| JP | 2010-160189 A | 7/2010 |
| JP | 2010-205986 A | 9/2010 |
| JP | 2011-116964 A | 6/2011 |
| JP | 2012-036357 A | 2/2012 |
| KR | 10-1042530 B1 | 6/2011 |
| WO | 2010/020329 A1 | 2/2010 |

OTHER PUBLICATIONS

Zhenan Bao et al., "Soluble and processable regioregular poly(3hexylthiophene) for thin film fieldeffect transistor applications with high mobility," Applied Physics Letters, vol. 69, 1996 pp. 4108-4110.

Machine generated English Translation of JP 2010-205986 published Sep. 16, 2010.

Machine generated English translation of JP 2009-022067 published Feb. 12, 2009.

Machine generated English translation of JP 2009-009964 published Jan. 15, 2009.

Machine generated English translation of JP 2009-182033 published Aug. 13, 2009.

Machine generated English translation of JP 2011-116964 published Jun. 16, 2011.

Torsten W. Bunnagel, et al., "Thiophene-Phenylene/Naphthalene-Based Step-Ladder Copolymers", Journal of Polymer Science: Part A: Polymer Chemistry, vol. 46, 2008, pp. 7342-7353.

Hugo Bronstein, et al., Synthesis of a Novel Fused Thiophene-thieno[3,2-b]thiophene-thiophene Donor monomer and Co-polymer for Use in OPV and OFETs, Macromolecular Rapid Communications, vol. 32, 2011, pp. 1664-1668.

ORGANIC SEMICONDUCTOR MATERIAL

TECHNICAL FIELD

The present invention relates to a compound and a polymer compound, and, an organic semiconductor material, an organic semiconductor device and an organic transistor containing the compound or the polymer compound.

BACKGROUND ART

Organic transistors are low in cost, and have properties such as flexibility, foldability and the like. Therefore, organic transistors are suitable for applications such as electronic paper, flexible displays and the like, and paid to attention recently.

Organic transistors have a layer having charge (denoting hole and electron, the same shall apply hereinafter) transportability constituted of an organic material, and as the organic material, organic semiconductor materials are mainly used.

As the performance of an organic transistor, electric field-effect mobility and the ON/OFF ratio are important and depend significantly on an organic semiconductor material used in the organic transistor. Therefore, an organic semiconductor material is required to have high mobility. If an organic semiconductor material is oxidized, the ON/OFF ratio of an organic transistor tends to lower, thus, stability against oxidation is also required. When an organic semiconductor material has high ionization potential, it is liable to be stable against oxidation.

As the organic semiconductor material used in an organic transistor, poly(3-hexylthiophene) as a polymer compound is suggested, and an organic transistor using the polymer compound shows an electric field-effect mobility of about $10^{-5}$ to $10^{-2}$ cm$^2$/Vs and an ON/OFF ratio of $10^4$ or less (non-patent document 1). The ionization potential of poly(3-hexylthiophene) is about 5.0 eV which is not necessarily recognized as high, thus, it is liable to be oxidized.

As the organic semiconductor material used in an organic transistor, the following polymer compound having a naphthalene structure, a thiophene structure and a benzothiadiazole structure is suggested, and the electric field-effect mobility of an organic transistor using the polymer compound is 0.003 cm$^2$/Vs (patent document 1).

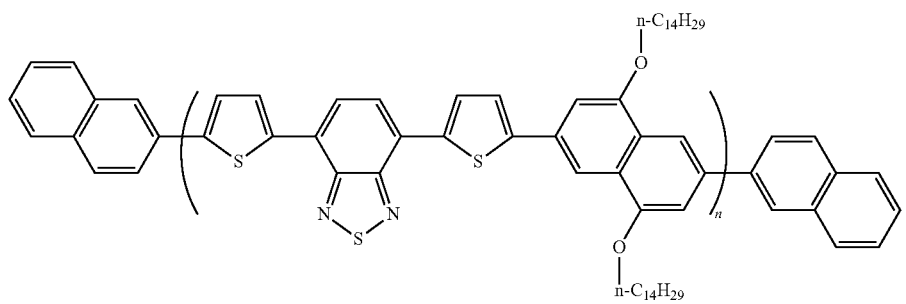

PRIOR ART DOCUMENT

Patent Document

[Patent document 1] Korean Patent Publication No. 10-1042530

Non-Patent Document

[Non-patent document 1] Applied Physics Letters, 1996, vol. 69, p. 4108

SUMMARY OF THE INVENTION

Problem to be Solved by the Invention

However, it is not recognized that an organic transistor using the above-described polymer compound attains both high electric field-effect mobility and high ON/OFF ratio as recently required.

Then, the present invention has also an object of providing a compound and a polymer compound useful for production of an organic transistor excellent in both electric field-effect mobility and the ON/OFF ratio. Further, the present invention has an object of providing an organic semiconductor material, an organic semiconductor device and an organic transistor containing the compound or the polymer compound.

Means for Solving the Problem

The present invention provides a compound and a polymer compound described below, and, an organic semiconductor material, an organic semiconductor device and an organic transistor containing the compound or the polymer compound.

[1] A compound represented by the formula (1):

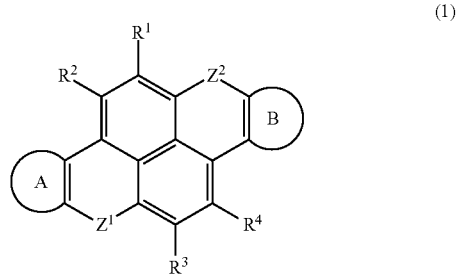

(1)

(wherein $R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by —B(OH)$_2$) or an organotin residue, and these groups may have a substituent.

The ring A and the ring B represent each independently a heterocyclic ring, and the heterocyclic ring may have a substituent.

$Z^1$ and $Z^2$ represent each independently one group selected from the group consisting of groups represented by the formula (Z-1) to the formula (Z-11).)

   (Z-1)

   (Z-2)

   (Z-3)

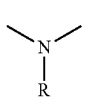   (Z-4)

   (Z-5)

   (Z-6)

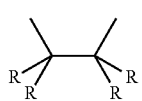   (Z-7)

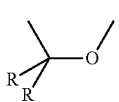   (Z-8)

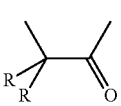   (Z-9)

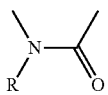   (Z-10)

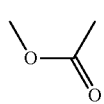   (Z-11)

(wherein R represents a hydrogen atom, an alkyl group, an alkoxy group, an alkylthio group, an aryl group, a mono-valent heterocyclic group or a halogen atom, and these groups may have a substituent. When a plurality of R are present, these may be the same or different.).

[2] The compound according to [1], wherein the above-described compound represented by the formula (1) is a compound represented by the formula (2):

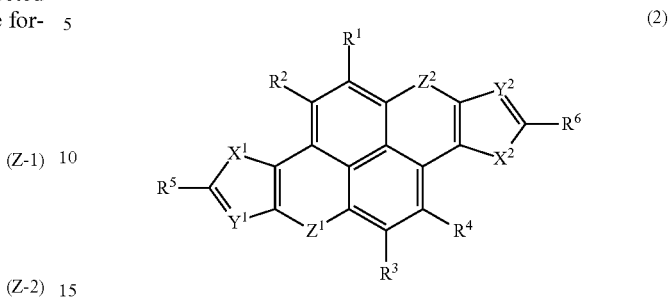   (2)

(wherein $R^1$, $R^2$, $R^3$, $R^4$, $Z^1$ and $Z^2$ represent the same meaning as described above.

$R^5$ and $R^6$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by —B(OH)$_2$) or an organotin residue, and these groups may have a substituent.

$X^1$ and $X^1$ represent each independently an oxygen atom, a sulfur atom or a selenium atom.

$Y^1$ and $Y^2$ represent each independently a nitrogen atom or a group represented by —CR$^7$=.

$R^7$ represents a hydrogen atom, an alkyl group, an alkoxy group, an alkylthio group, an aryl group, a mono-valent heterocyclic group or a halogen atom.).

[3] A polymer compound comprising a structural unit represented by the formula (3):

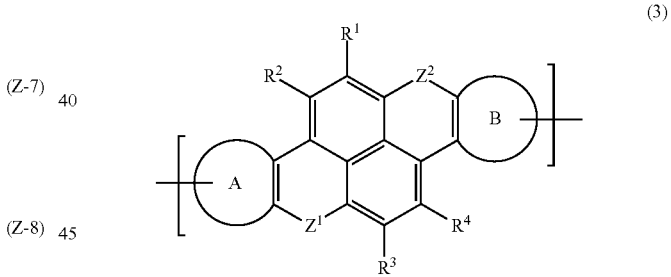   (3)

(wherein $R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by —B(OH)$_2$) or an organotin residue, and these groups may have a substituent.

The ring A and the ring B represent each independently a heterocyclic ring, and the aromatic ring may have a substituent.

$Z^1$ and $Z^2$ represent each independently one group selected from the group consisting of groups represented by the formula (Z-1) to the formula (Z-11).)

   (Z-1)

 (Z-2)

 (Z-3)

 (Z-4)

 (Z-5)

 (Z-6)

 (Z-7)

 (Z-8)

 (Z-9)

 (Z-10)

 (Z-11)

(wherein R represents a hydrogen atom, an alkyl group, an alkoxy group, an alkylthio group, an aryl group, a mono-valent heterocyclic group or a halogen atom, and these groups may have a substituent. When a plurality of R are present, these may be the same or different.).

[4] The compound according to [3], wherein the above-described structural unit represented by the formula (3) is a structural unit represented by the formula (4):

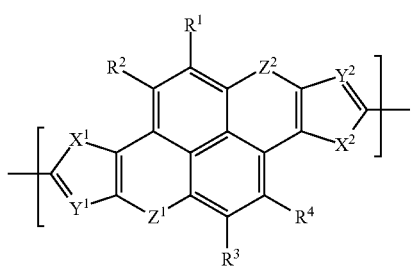 (4)

(wherein $R^1$, $R^2$, $R^3$, $R^4$, $Z^1$ and $Z^2$ represent the same meaning as described above.

$R^5$ and $R^6$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by $-B(OH)_2$) or an organotin residue, and these groups may have a substituent.

$X^1$ and $X^2$ represent each independently an oxygen atom, a sulfur atom or a selenium atom.

$Y^1$ and $Y^2$ represent each independently a nitrogen atom or a group represented by $-CR^7=$.

$R^7$ represents a hydrogen atom, an alkyl group, an alkoxy group, an alkylthio group, an aryl group, a mono-valent heterocyclic group or a halogen atom.).

[5] The compound or polymer compound according to any one of [1] to [4], wherein the above-described $X^1$ and the above-described $X^2$ are a sulfur atom.

[6] The compound or polymer compound according to any one of [1] to [5], wherein the above-described $Y^1$ and the above-described $Y^2$ are a group represented by $-CH=$.

[7] The compound or polymer compound according to any one of [1] to [6], wherein the above-described $Z^1$ and the above-described $Z^2$ are a group represented by the formula (Z-1).

The polymer compound according to any one of [3] to [7], further comprising a structural unit represented by the formula (5).

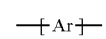 (5)

(wherein Ar represents an arylene group or a di-valent heterocyclic group, and these groups may have a substituent, with the proviso that Ar is different from the above-described structural unit represented by the formula (3).)

[9] The polymer compound according to [8], wherein the above-described structural unit represented by the formula (5) is a structural unit represented by the formula (6):

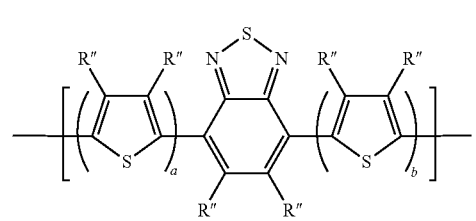 (6)

(wherein R" represents a hydrogen atom, an alkyl group, an aryl group, a mono-valent heterocyclic group or a halogen atom. A plurality of R' may be the same or different.

a and b represent each independently an integer of 0 to 5.).

[10] The polymer compound according to [9], wherein the polymer compound is a copolymer of the above-described structural unit represented by the formula (3) and the above-described structural unit represented by the formula (6).

[11] An organic semiconductor material, comprising the compound or polymer compound according to any one of [1] to [10].

[12] An organic semiconductor device, comprising an organic layer comprising the organic semiconductor material according to [11].

[13] An organic transistor comprising a source electrode, a drain electrode, a gate electrode and an active layer, wherein the active layer comprises the organic semiconductor material according to [11].

MODES FOR CARRYING OUT THE INVENTION

Figure 1:
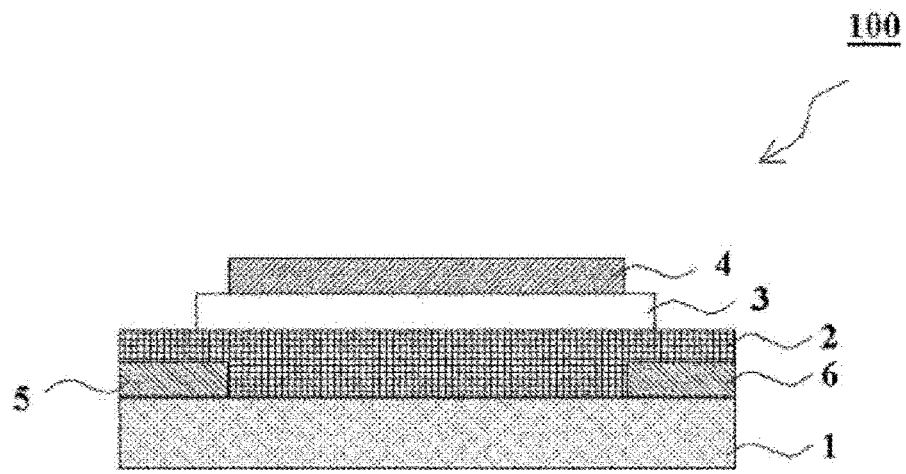
FIG. 1 is a schematic cross-sectional view showing one example of the organic transistor of the present invention.

Suitable embodiments of the present invention will be illustrated in detail below, if necessary, referring to drawings. In explanations of drawings, the same elements are attached with the same marks, and overlapping explanations will be omitted.
<Compound Represented by the Formula (1)>
The compound of the present invention is a compound represented by the formula (1).

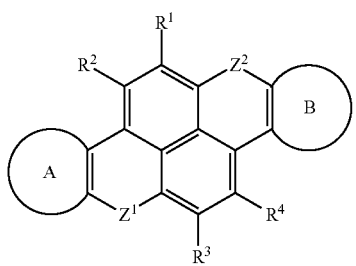

(1)

In the formula (1), $R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by $—B(OH)_2$) or an organotin residue, and these groups may have a substituent.

The alkyl group represented by $R^1$ may be any of a linear alkyl group and a branched alkyl group, and may also be a cycloalkyl group. The number of carbon atoms of the alkyl group is usually 1 to 30 (in the case of the branched alkyl group and cycloalkyl group, usually 3 to 30), preferably 1 to 20 (in the case of the branched alkyl group and cycloalkyl group, 3 to 20). The above-described number of carbon atoms does not include the number of carbon atoms of a substituent.

Specific examples of the alkyl group include linear alkyl groups such as a methyl group, an ethyl group, a n-propyl group, a n-butyl group, a n-hexyl group, a n-octyl group, a n-dodecyl group, a n-hexadecyl group and the like, branched alkyl groups such as an isopropyl group, an isobutyl group, a sec-butyl group, a tert-butyl group, a 2-ethylhexyl group, a 3,7-dimethyloctyl group and the like, and cycloalkyl groups such as a cyclopentyl group, a cyclohexyl group and the like.

The alkyl group may have a substituent, and the substituent which the alkyl group may have includes an alkoxy group, an aryl group, a halogen atom and the like. Specific examples of the alkyl group having a substituent includes a methoxyethyl group, a benzyl group, a trifluoromethyl group, a perfluorohexyl group and the like.

The alkoxy group represented by $R^1$ may be any of a linear alkoxy group and a branched alkoxy group, and may also be a cycloalkoxy group. The number of carbon atoms of the alkoxy group is usually 1 to 30 (in the case of the branched alkoxy group and cycloalkoxy group, usually 3 to 30), preferably 1 to 20 (in the case of the branched alkoxy group and cycloalkoxy group, 3 to 20). The above-described number of carbon atoms does not include the number of carbon atoms of a substituent.

Specific examples of the alkoxy group include, linear alkoxy groups such as a methoxy group, an ethoxy group, a n-propyloxy group, a n-butyloxy group, a n-hexyloxy group, a n-octyloxy group, a n-dodecyloxy group, a n-hexadecyloxy group and the like, branched alkoxy groups such as an isopropyloxy group, an isobutyloxy group, a sec-butyloxy group, a tert-butyloxy group, a 2-ethylhexyloxy group, a 3,7-dimethyloctyloxy group and the like, and cycloalkoxy groups such as a cyclopentyloxy group, a cyclohexyloxy group and the like.

The alkoxy group may have a substituent, and the substituent which the alkoxy group may have includes an alkoxy group, an aryl group, a halogen atom and the like.

The alkylthio group represented by $R^1$ may be any of a linear alkylthio group and a branched alkylthio group, and may also be a cycloalkylthio group. The number of carbon atoms of the alkylthio group is usually 1 to 30 (in the case of the branched alkylthio group and cycloalkylthio group, usually 3 to 30), preferably 1 to 20 (in the case of the branched alkylthio group and cycloalkylthio group, 3 to 20). The above-described number of carbon atoms does not include the number of carbon atoms of a substituent.

Specific examples of the alkylthio group include linear alkylthio groups such as a methylthio group, an ethylthio group, a n-propylthio group, a n-butylthio group, a n-hexylthio group, a n-octylthio group, a n-dodecylthio group, a n-hexadecylthio group and the like, branched alkylthio groups such as an isopropylthio group, an isobutylthio group, a sec-butylthio group, a tert-butylthio group, a 2-ethylhexylthio group, a 3,7-dimethyloctylthio group and the like, and cycloalkylthio groups such as a cyclopentylthio group, a cyclohexylthio group and the like.

The alkylthio group may have a substituent, and the substituent which the alkylthio group may have includes an alkoxy group, an aryl group, a halogen atom and the like.

The aryl group represented by $R^1$ is an atomic group remaining after removing, from an aromatic hydrocarbon which may have a substituent, one hydrogen atom bonded directly to a carbon atom constituting the ring, and includes groups having a condensed ring and groups obtained by directly bonding two rings selected from the group consisting of independent benzene rings and condensed rings.

The number of carbon atoms of the aryl group is usually 6 to 30, preferably 6 to 20. The above-described number of carbon atoms does not include the number of carbon atoms of a substituent.

Specific examples of the aryl group include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 4-phenylphenyl group and the like.

The aryl group may have a substituent, and the substituent which the aryl group may have includes an alkyl group, an alkoxy group, an alkylthio group, a mono-valent heterocyclic group, a halogen atom and the like. The aryl group having a substituent includes a 4-hexadecylphenyl group, a 3,5-dimethoxyphenyl group, a pentafluorophenyl group and the like. When the aryl group has a substituent, the substituent is preferably an alkyl group.

The mono-valent heterocyclic group represented by $R^1$ is an atomic group remaining after removing, from a heterocyclic compound which may have a substituent, one hydrogen atom bonded directly to a carbon atom constituting the ring, and includes groups having a condensed ring and groups obtained by directly bonding two or more rings selected from the group consisting of independent heterocyclic rings and condensed rings. The number of carbon atoms of the mono-valent heterocyclic group is usually 2 to 30, preferably 3 to 20. The above-described number of carbon atoms does not include the number of carbon atoms of a substituent.

Specific examples of the mono-valent heterocyclic group include a 2-furyl group, a 3-furyl group, a 2-thienyl group, a 3-thienyl group, a 2-pyrrolyl group, a 3-pyrrolyl group, a 2-oxazolyl group, a 2-thiazolyl group, a 2-imidazolyl group, a 2-pyridyl group, a 3-pyridyl group, a 4-pyridyl group, a 2-benzofuryl group, a 2-benzothienyl group, a 2-thienothienyl group, a 4-(2,1,3-benzothiadiazolyl) group and the like.

The mono-valent heterocyclic group may have a substituent, and the substituent which the mono-valent heterocyclic group may have includes an alkyl group, an alkoxy group, an alkylthio group, an aryl group, a halogen atom and the like. The mono-valent heterocyclic group having a substituent includes a 5-octyl-2-thienyl group, a 5-phenyl-2-furyl group and the like. When the mono-valent heterocyclic group has a substituent, the substituent is preferably an alkyl group.

The halogen atom represented by $R^1$ includes fluorine atom, a chlorine atom, a bromine atom and an iodine atom.

The silyl group represented by $R^1$ may have a substituent. The substituent which the silyl group may have includes an alkyl group, an aryl group and the like. The silyl group having a substituent includes a trimethylsilyl group, a triethylsilyl group, a triisopropylsilyl group, a tert-butyldimethylsilyl group, a phenylsilyl group, a triphenylsilyl group and the like.

The amino group represented by $R^1$ may have a substituent. The substituent which the amino group may have includes an alkyl group, an aryl group and the like. The amino group having a substituent includes a dimethylamino group, a diethylamino group, a diisopropylamino group, a diphenylamino group and the like.

The alkenyl group represented by $R^1$ may be any of a linear alkenyl group and a branched alkenyl group, and may also be a cycloalkenyl group. The number of carbon atoms of the alkenyl group is usually 2 to 30 (in the case of the branched alkenyl group and cycloalkenyl group, usually 3 to 30), preferably 2 to 20 (in the case of the branched alkenyl group and cycloalkenyl group, 3 to 20). The above-described number of carbon atoms does not include the number of carbon atoms of a substituent.

Specific examples of the alkenyl group include a vinyl group, a 1-propenyl group, a 2-propenyl group, a 1-hexenyl group, a 1-dodecenyl group, a 1-hexadecenyl group, a 1-cyclohexenyl group and the like.

The alkenyl group may have a substituent, and the substituent which the alkenyl group may have includes an aryl group, a halogen atom, a silyl group and the like.

The alkynyl group represented by $R^1$ may be any of a linear alkynyl group and a branched alkynyl group.

The number of carbon atoms of the alkynyl group is usually 2 to 30 (in the case of the branched alkynyl group, usually 4 to 30), preferably 2 to 20 (in the case of the branched alkynyl group, 4 to 20).

The above-described number of carbon atoms does not include the number of carbon atoms of a substituent.

Specific examples of the alkynyl group include an ethynyl group, a 1-propynyl group, a 1-hexynyl group, a 1-dodecynyl group, a 1-hexadecynyl group and the like.

The alkynyl group may have a substituent, and the substituent which the alkynyl group may have includes an aryl group, a halogen atom, a silyl group and the like.

The alkylcarbonyl group represented by $R^1$ includes groups obtained by linking the above-described alkyl group with a carbonyl group.

Specific examples of the alkylcarbonyl group include linear alkylcarbonyl groups such as an acetyl group, a n-propanoyl group, a n-butanoyl group, a n-hexanoyl group, a n-octanoyl group, a n-dodecanoyl group, a n-hexadecanoyl group and the like, branched alkylcarbonyl groups such as an isobutanoyl group, a sec-butanoyl group, a tert-butanoyl group, a 2-ethylhexanoyl group and the like, and cycloalkylcarbonyl groups such as a cyclopentylcarbonyl group, a cyclohexylcarbonyl group and the like.

The above-described alkoxycarbonyl; group represented by $R^1$ includes groups obtained by linking the above-described alkoxy group with a carbonyl group.

Specific examples of the alkoxycarbonyl group include linear alkoxycarbonyl groups such as a methoxycarbonyl group, an ethoxycarbonyl group, a n-propyloxycarbonyl group, a n-butoxycarbonyl group, a n-hexyloxycarbonyl group, a n-octyloxycarbonyl group, a n-dodecyloxycarbonyl group, a n-hexadecyloxycarbonyl group and the like, branched alkoxycarbonyl groups such as an isopropyloxycarbonyl group, an isobutyloxycarbonyl group, a sec-butyloxycarbonyl group, a tert-butyloxycarbonyl group, a 2-ethylhexyloxycarbonyl group and the like, and cycloalkoxycarbonyl groups such as a cyclopentyloxycarbonyl group, a cyclohexyloxycarbonyl group and the like.

The borate residue represented by $R^1$ includes groups represented by the following formulae:

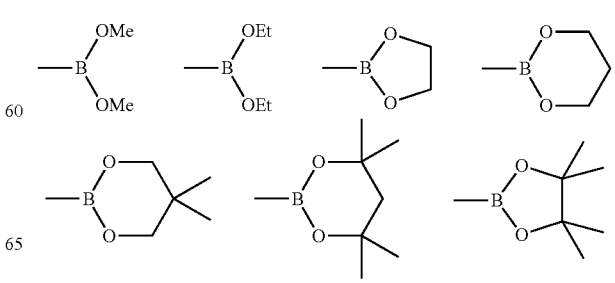

-continued

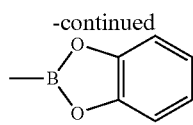

(wherein Me represents a methyl group and Et represents an ethyl group.).

The organotin residue represented by $R^1$ includes groups represented by $—SnR^T_3$ and the like. Here, $R^T$ represents an alkyl group or an aryl group, preferably an alkyl group.

Specific examples of the organotin residue include $—SnMe_3$, $—SnEt_3$, $—SnBu_3$ and $SnPh_3$, preferably $—SnMe_3$, $—SnEt_3$ or $SnBu_3$. Here, Me represents a methyl group, Et represents an ethyl group, Bu represents a butyl group, and Ph represents a phenyl group.

The definitions and specific examples of the alkyl group, alkoxy group, alkylthio group, aryl group, mono-valent heterocyclic group, halogen atom, silyl group, amino group, alkenyl group, alkynyl group, alkylcarbonyl group, alkoxycarbonyl group, borate residue or organotin residue represented by $R^2$, $R^3$ and $R^4$ are the same as the definitions and specific examples of the above-described alkyl group, alkoxy group, alkylthio group, aryl group, mono-valent heterocyclic group, halogen atom, silyl group, amino group, alkenyl group, alkynyl group, alkylcarbonyl group, alkoxycarbonyl group, borate residue or organotin residue represented by $R^1$.

From the standpoint of further enhancing the electric field-effect mobility and the ON/OFF ratio of an organic transistor produced by using the compound of the present invention, $R^1$, $R^2$, $R^3$ and $R^4$ represents preferably a hydrogen atom, an alkyl group, an alkoxy group, an alkylthio group, a halogen atom, an alkenyl group or an alkynyl group, more preferably a hydrogen atom, an alkyl group, a halogen atom, an alkenyl group or an alkynyl group, further preferably a hydrogen atom.

In the formula (1), the ring A and the ring B represent each independently a heterocyclic ring, and the heterocyclic ring may have a substituent. The number of carbon atoms of the heterocyclic ring is preferably 2 to 30, more preferably 2 to 14, further preferably 3 to 8. The above-described number of carbon atoms does not include the number of carbon atoms of a substituent.

Specific examples of the heterocyclic ring include a furan ring, a thiophene ring, a selenophene ring, a pyrrole ring, an oxazole ring, a thiazole ring, an imidazole ring, a pyridine ring, a benzofuran ring, a benzothiophene ring, a thienothiophene ring, a 2,1,3-benzothiadiazole ring, and the like.

The substituent which the heterocyclic ring may have includes an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by $—B(OH)_2$) or an organotin residue and the like, and the definitions and specific examples of the substituent are the same as the definitions and specific examples of the above-described alkyl group, alkoxy group, alkylthio group, aryl group, mono-valent heterocyclic group, halogen atom, silyl group, amino group, alkenyl group, alkynyl group, alkylcarbonyl group, alkoxycarbonyl group, borate residue or organotin residue represented by $R^1$.

From the standpoint of easiness of synthesis of the compound of the present invention, it is preferable that the ring A and the ring B represent the same heterocyclic ring.

From the standpoint of further enhancing the electric field-effect mobility and the ON/OFF ratio of an organic transistor produced by using the compound of the present invention, the ring A and the ring B represent preferably a 5 to 6-membered ring, more preferably a 5-membered ring.

In the formula (1), $Z^1$ and $Z^2$ represent each independently one group selected from the group consisting of groups represented by the formula (Z-1) to the formula (Z-11).

From the standpoint of easiness of synthesis of the compound of the present invention, it is preferable that $Z^1$ and $Z^2$ represent the same group.

From the standpoint of enhancing the electric field-effect mobility and the ON/OFF ratio of an organic transistor produced by using the compound of the present invention, $Z^1$ and $Z^2$ are preferably a group represented by the formula (Z-1) to the formula (Z-5), more preferably a group represented by the formula (Z-1) to the formula (Z-3), further preferably a group represented by the formula (Z-1).

In the formulae (Z-1) to (Z-11), R represents a hydrogen atom, an alkyl group, an alkoxy group, an alkylthio group, an aryl group, a mono-valent heterocyclic group or a halogen atom, and these groups may have a substituent.

The definitions and specific examples of the alkyl group, alkoxy group, alkylthio group, aryl group, mono-valent heterocyclic group or halogen atom are the same as the definitions and specific examples of the above-described alkyl group, alkoxy group, alkylthio group, aryl group, mono-valent heterocyclic group or halogen atom represented by $R^1$.

From the standpoint of further enhancing the electric field-effect mobility and the ON/OFF ratio of an organic transistor produced by using the compound of the present invention, R represents preferably a hydrogen atom, an alkyl group or an aryl group, more preferably an alkyl group or an aryl group.

From the standpoint of easiness of synthesis of the compound of the present invention, the compound represented by the formula (1) is preferably a compound represented by the formula (2).

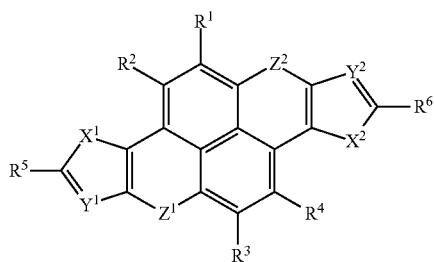

(2)

(wherein $R^1$, $R^2$, $R^3$, $R^4$, $Z^1$ and $Z^2$ represent the same meaning as described above.

$R^5$ and $R^6$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by —B(OH)$_2$) or an organotin residue, and these groups may have a substituent.

$X^1$ and $X^2$ represent each independently an oxygen atom, a sulfur atom or a selenium atom.

$Y^1$ and $Y^2$ represent each independently a nitrogen atom or a group represented by —CR$^7$=.

$R^7$ represents a hydrogen atom, an alkyl group, an alkoxy group, an alkylthio group, an aryl group, a mono-valent heterocyclic group or a halogen atom.).

The definitions and specific examples of the alkyl group, alkoxy group, alkylthio group, aryl group, mono-valent heterocyclic group, halogen atom, silyl group, amino group, alkenyl group, alkynyl group, alkylcarbonyl group, alkoxycarbonyl group, borate residue or organotin residue represented by $R^5$ and $R^6$ are the same as the definitions and specific examples of the above-described alkyl group, alkoxy group, alkylthio group, aryl group, mono-valent heterocyclic group, halogen atom, silyl group, amino group, alkenyl group, alkynyl group, alkylcarbonyl group, alkoxycarbonyl group, borate residue or organotin residue represented by $R^1$.

From the standpoint of further enhancing the electric field-effect mobility and the ON/OFF ratio of an organic transistor produced by using the compound of the present invention, $R^5$ and $R^6$ represent preferably a hydrogen atom, an alkyl group, an aryl group, a mono-valent heterocyclic group, a halogen atom, an alkenyl group or an alkynyl group, more preferably a hydrogen atom, an alkyl group, an aryl group or a mono-valent heterocyclic group.

From the standpoint of use as a raw material compound for obtaining the polymer compound of the present invention, $R^5$ and $R^6$ represent preferably a halogen atom, a borate residue, a boric acid residue (denoting a group represented by —B(OH)$_2$) or an organotin residue, more preferably a bromine atom, an iodine atom, a borate residue, a boric acid residue (denoting a group represented by —B(OH)$_2$) or an organotin residue.

From the standpoint of easiness of synthesis of the compound of the present invention, $X^1$ and $X^2$ represent preferably an oxygen atom or a sulfur atom, more preferably a sulfur atom.

From the standpoint of easiness of synthesis of the compound of the present invention, $Y^1$ and $Y^2$ represent preferably —CR$^7$=, more preferably —CH=.

Preferable specific examples of the compound represented by the formula (1) include, for example, compounds represented by the following formula (1-1) to formula (1-55).

Compounds represented by the formula (1-1) to the formula (1-7) or the formula (1-13) to the formula (1-55) are preferable, compounds represented by the formula (1-1) to the formula (1-6) or the formula (1-13) to the formula (1-24) are more preferable, compounds represented by the formula (1-1), the formula (1-2), the formula (1-5), the formula (1-13), the formula (1-14), the formula (1-17), the formula (1-18), the formula (1-21) or the formula (1-22) are further preferable, in which the ring A and the ring B represent a 5-membered ring, since the electric field-effect mobility and the ON/OFF ratio of an organic transistor produced by using the compound of the present invention are more excellent.

When the polymer compound of the present invention described later is produced by using the compound of the present invention, compounds represented by the formula (1-36) to the formula (1-55) are preferable, and compounds represented by the formula (1-36) to the formula (1-44) or the formula (1-48) to the formula (1-53) in which $Z^1$ and $Z^2$ are presented by the formula (Z-1) are more preferable, since the electric field-effect mobility and the ON/OFF ratio of an organic transistor produced by using the polymer compound are more excellent.

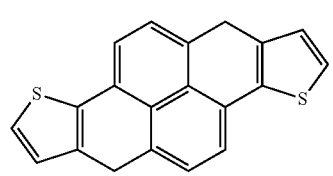

1-1

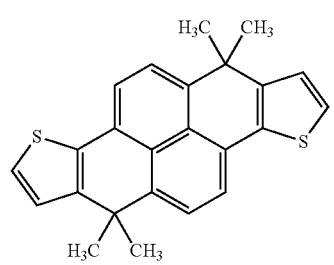

1-2

-continued
1-3
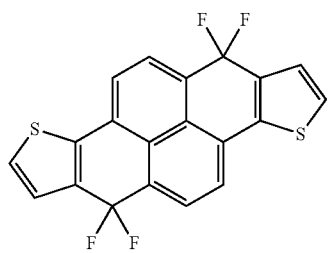
1-4
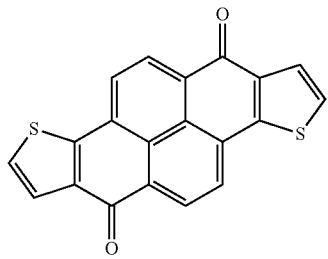
1-5
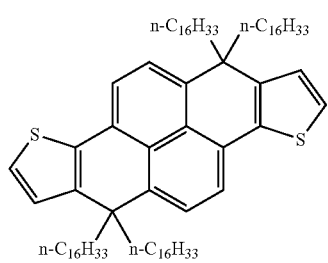
1-6
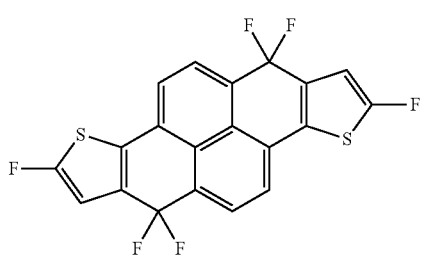
1-7
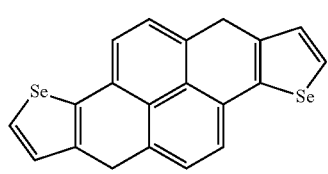
1-8
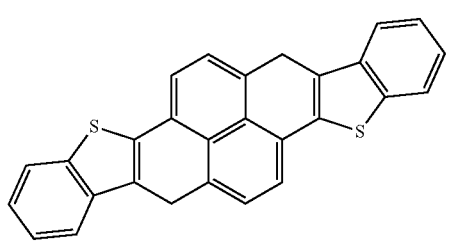
1-9
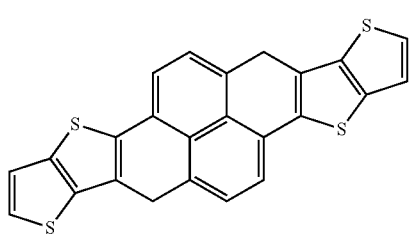
1-10
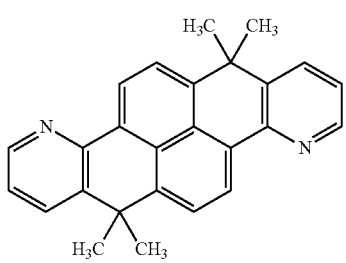
1-11
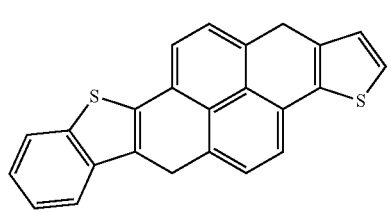
1-12
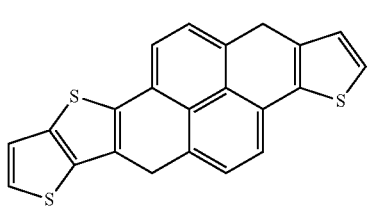
1-13
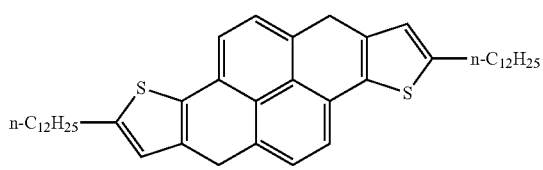
1-14
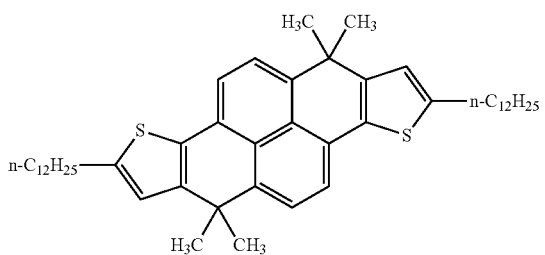

-continued
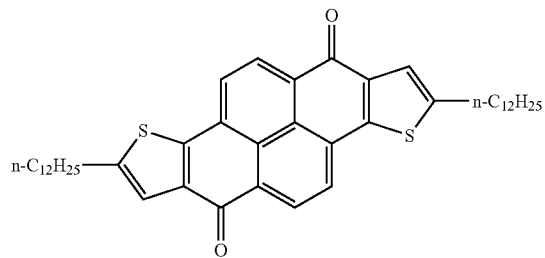
1-15
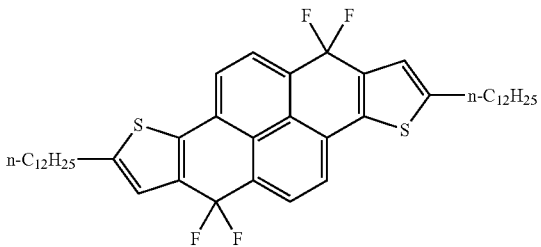
1-16
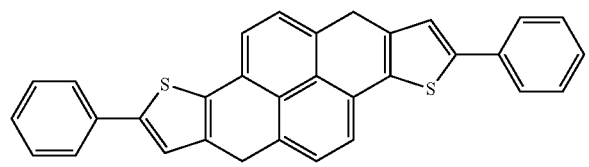
1-17
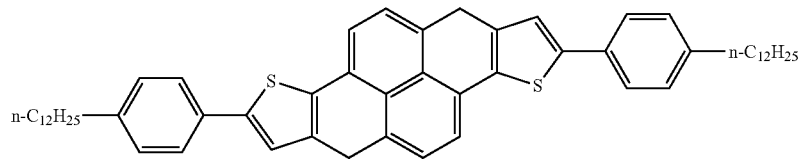
1-18
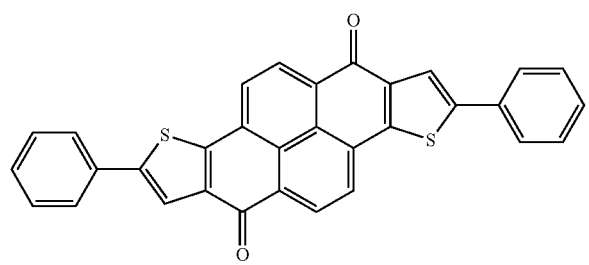
1-19
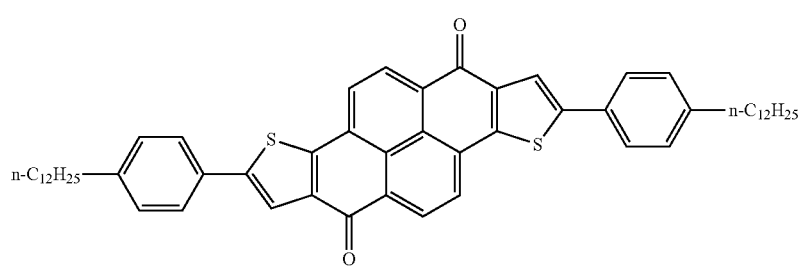
1-20
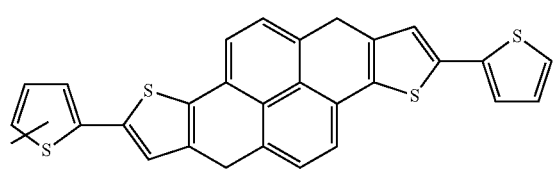
1-21
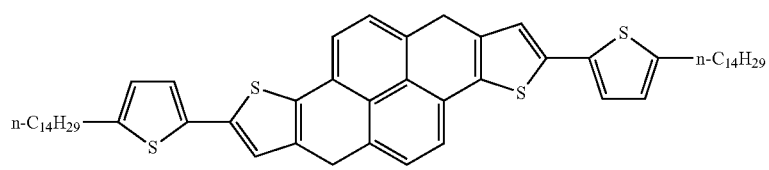
1-22

-continued
1-23
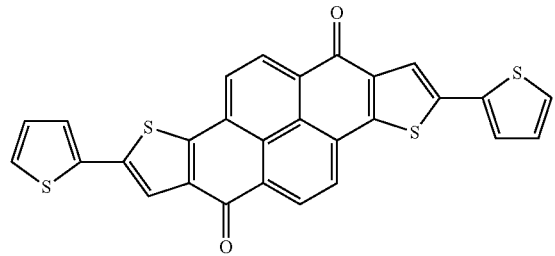
1-24
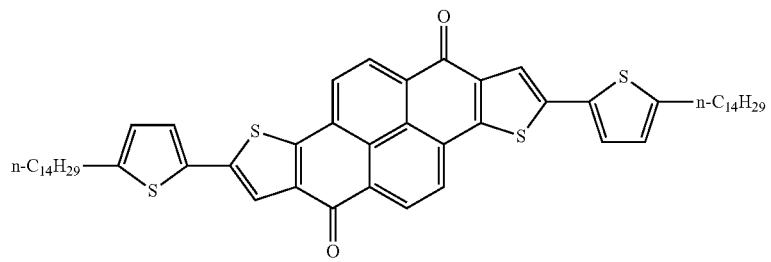
1-25
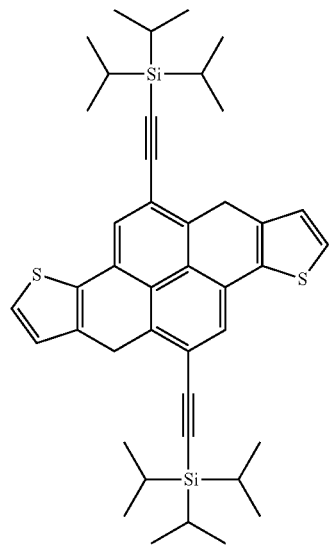
1-26
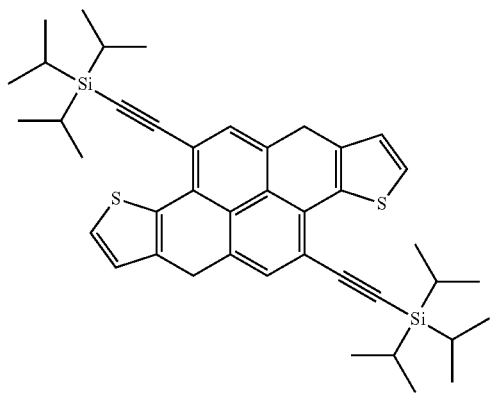
1-27
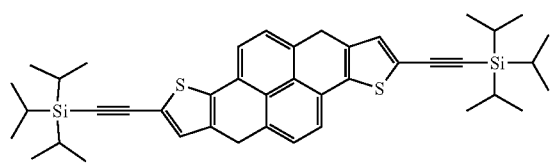
1-28
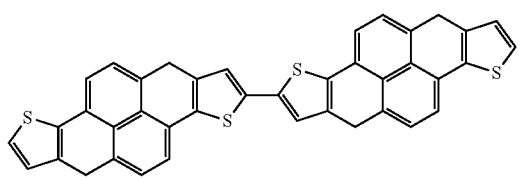
1-29
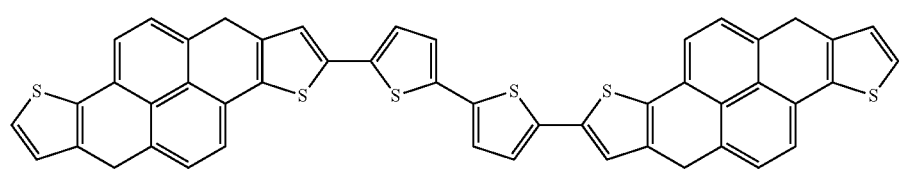

-continued
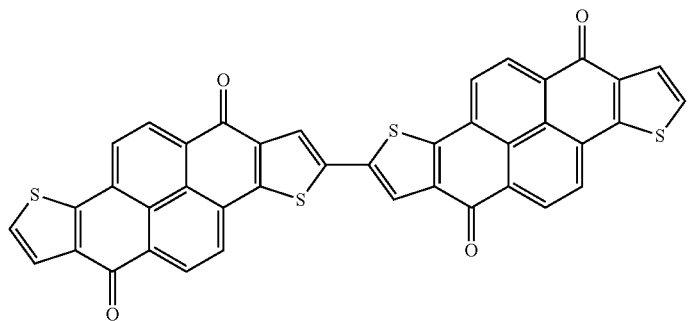
1-30
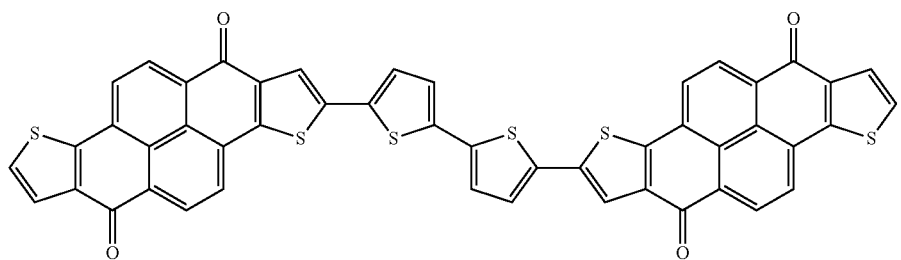
1-31
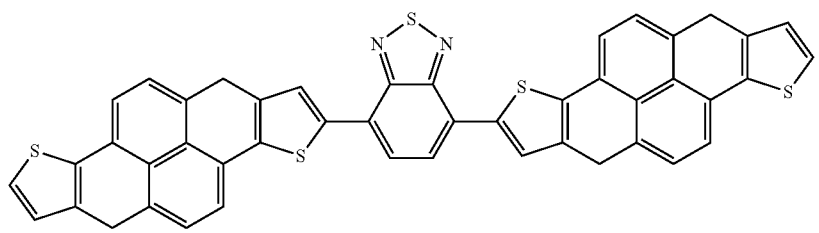
1-32
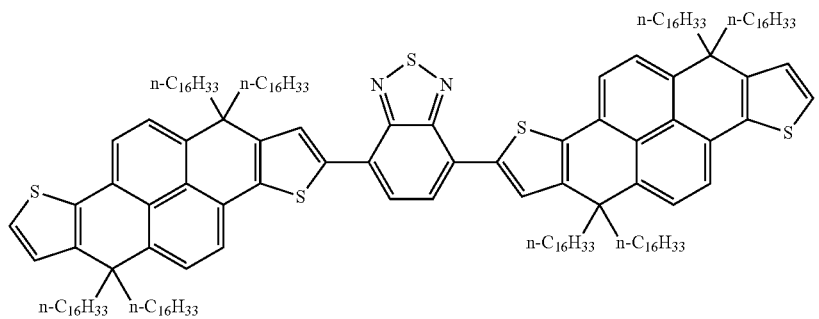
1-33
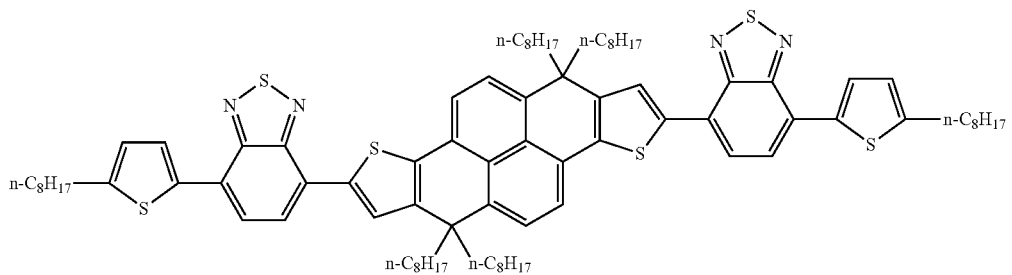
1-34

-continued
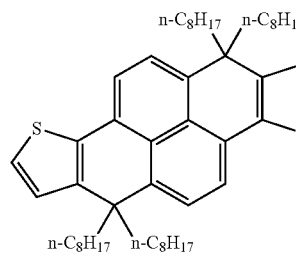
1-35
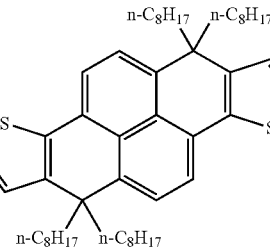
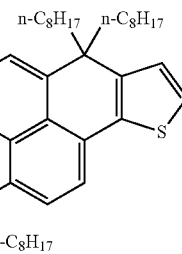
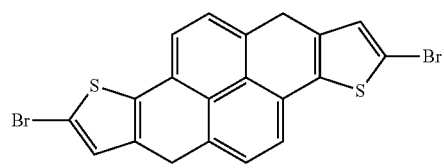
1-36
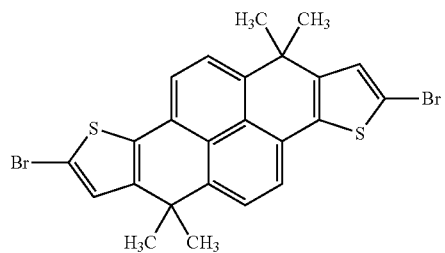
1-37
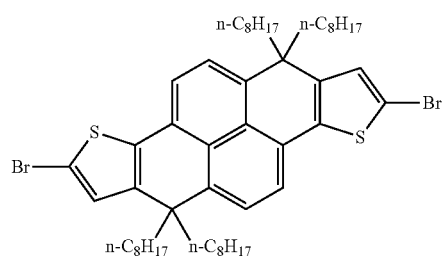
1-38
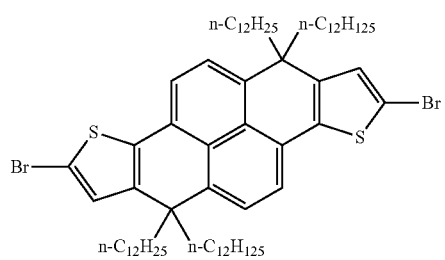
1-39
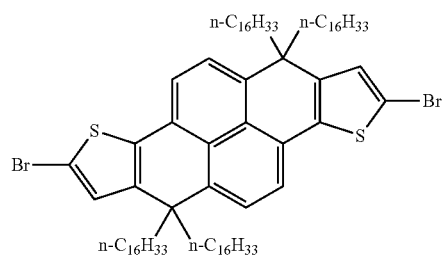
1-40
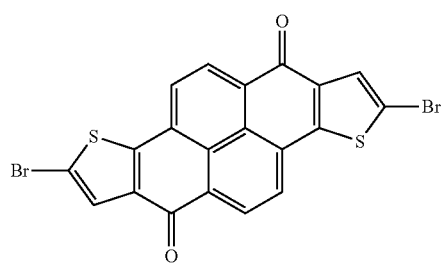
1-41
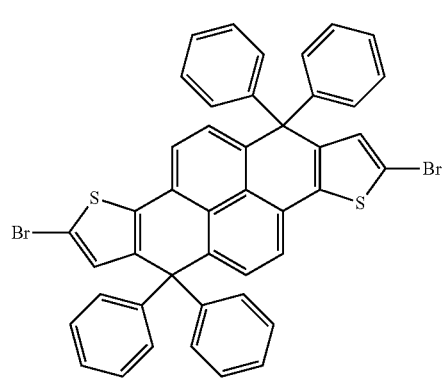
1-42
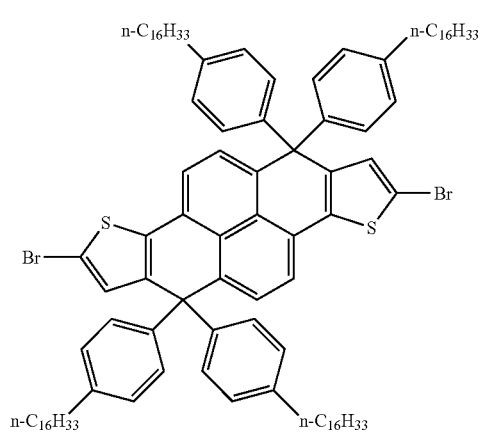
1-43

-continued
1-44
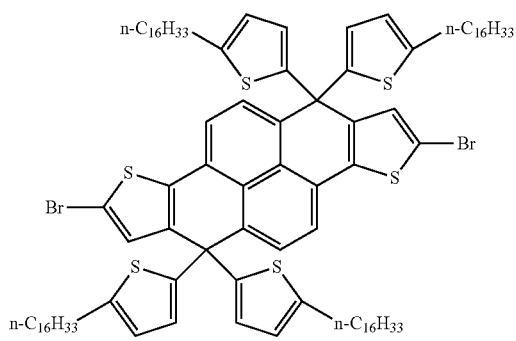
1-45
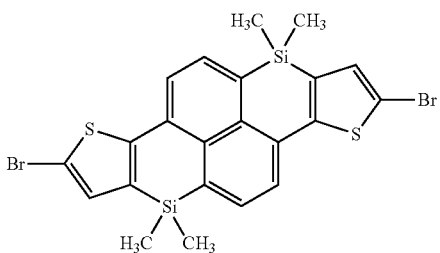
1-46
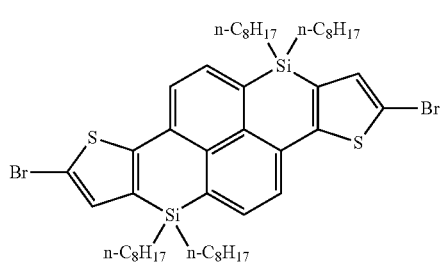
1-47
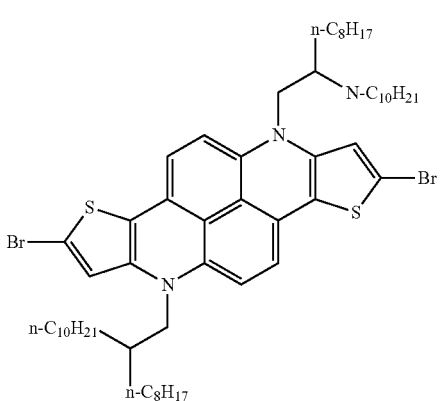
1-48
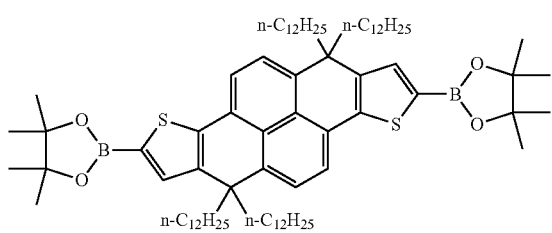
1-49
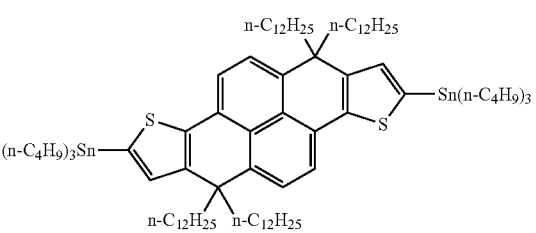
1-50
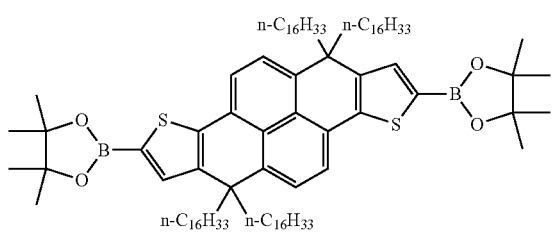
1-51
1-52
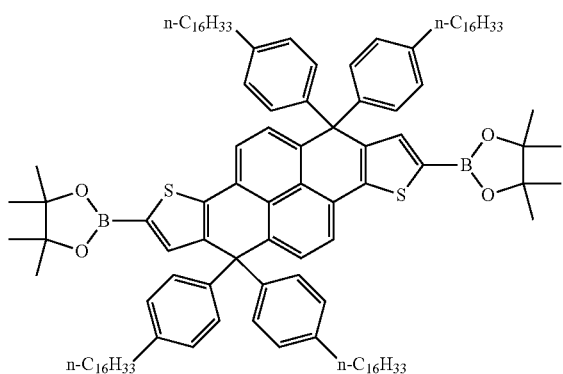
1-53
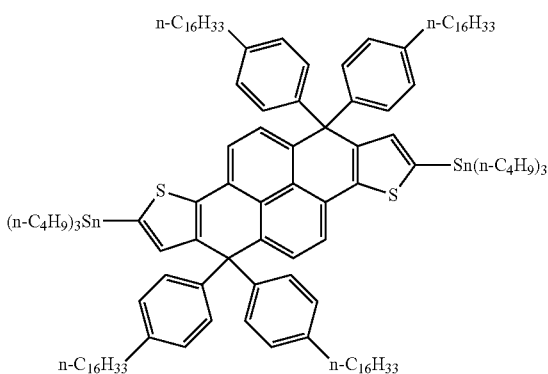

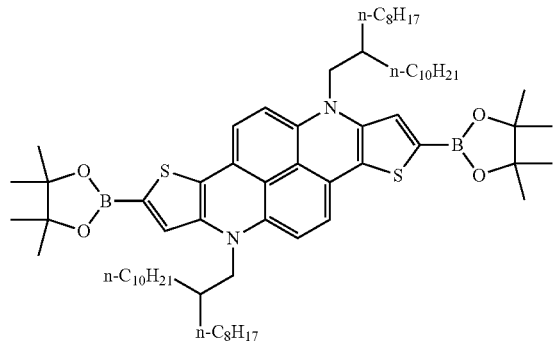

1-54

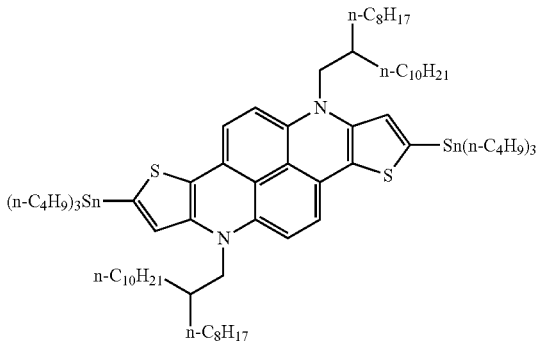

1-55

<Method of Producing Compound>

Next, a method of producing a compound represents by the formula (1) will be illustrated.

The compound represented by the formula (1) may be produced by any methods, and for example, can be produced by bromination, Suzuki coupling, Wolff-Kishner reduction, Buchwald-Hartwig amination, oxidative cyclization and the like as explained below.

When $Z^1$ and $Z^2$ are a group represented by the formula (Z-5), the compound represented by the formula (1) can be produced, for example, by a first step of reacting a compound represented by the formula (s1), a compound represented by the formula (s2) and a compound represented by the formula (s3) according to the Suzuki coupling reaction, and a second step of intramolecular-cyclizing the compound represented by the formula (s4) obtained in the first step. The compound obtained in this case is a compound represented by the formula (s5).

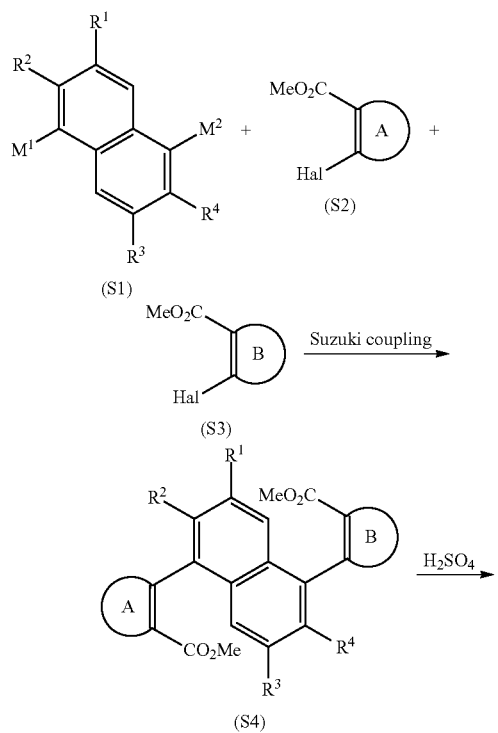

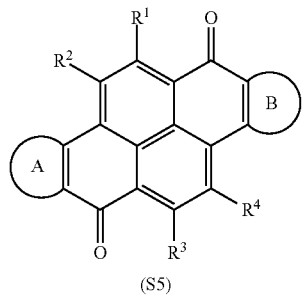

(S5)

(wherein $R^1$, $R^2$, $R^3$, $R^4$, ring A and ring B represent the same meaning as described above.

$M^1$ and $M^2$ represent each independently a borate residue or a boric acid residue (denoting a group represented by $-B(OH)_2$).

Each of Hal represents independently an iodine atom, a bromine atom or a chlorine atom.)

When $Z^1$ and $Z^2$ are a group represented by the formula (Z-1), the compound represented by the formula (1) can be produced, for example, by a first step of reacting the above-described compound represented by the formula (s5) according to the Wolff-Kishner reduction, and a second step of reacting the compound represented by the formula (s6) obtained in the first step, a base such as sodium alkoxide and the like, and an alkyl halide. The compound obtained in this case is a compound represented by the formula (s7).

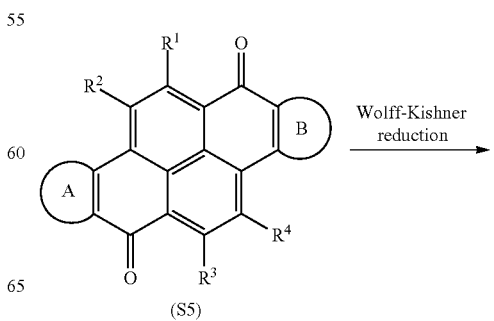

(S5)

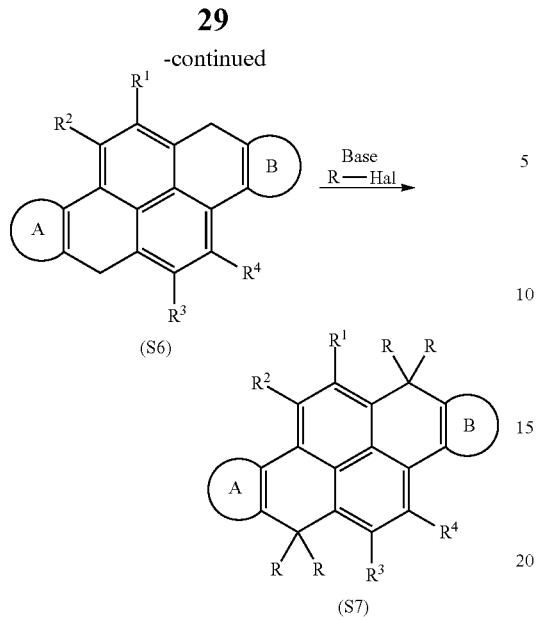

(wherein $R^1$, $R^2$, $R^3$, $R^4$, R, ring A, ring B and Hal represent the same meaning as described above.)

When $Z^1$ and $Z^2$ are a group represented by the formula (Z-1), the compound represented by the formula (1) can be produced, as another method, by a first step of reacting a compound represented by the formula (s1), a compound represented by the formula (s8) and a compound represented by the formula (s9) according to the Suzuki coupling reaction, a second step of reacting the compound represented by the formula (s10) obtained in the first step and butyllithium to lithiate the compound, and further reacting with a ketone, and a third step of reacting the compound represented by the formula (s11) obtained in the second step and an acid such as trifluoroboric acid, sulfuric acid and the like to cyclize the compound. The compound obtained in this case is a compound represented by the formula (s7).

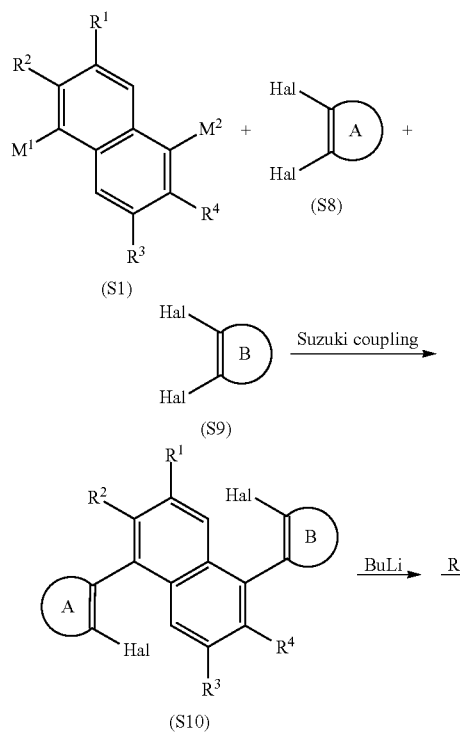

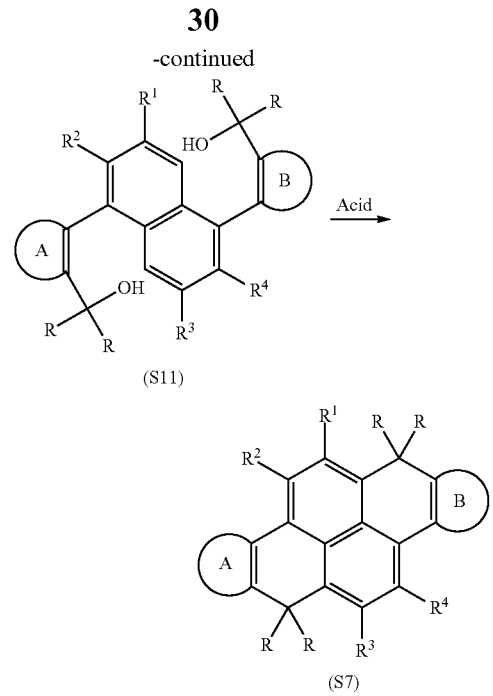

(wherein $R^1$, $R^2$, $R^3$, $R^4$, R, $M^1$, $M^2$, ring A, ring B and Hal represent the same meaning as described above.)

When $Z^1$ and $Z^2$ are a group represented by the formula (Z-2) or the formula (Z-3), the compound represented by the formula (1) can be produced, for example, by a first step of reacting the above-described compound represented by the formula (s10) and a halogenating agent such as N-bromosuccinimide and the like, a second step of reacting the compound represented by the formula (s12) obtained in the first step and butyllithium to lithiate the compound, and further reacting with a compound represented by $R_2ECl_2$ and the like. The compound obtained in this case is a compound represented by the formula (s13).

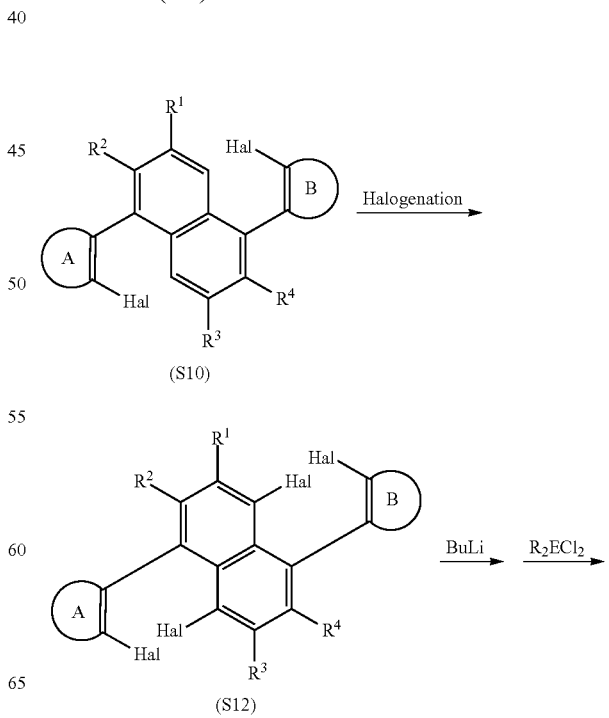

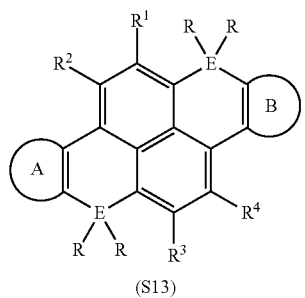

(S13)

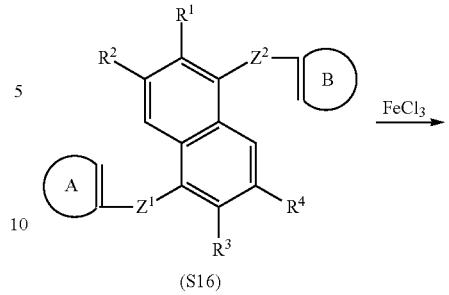

(S16)

(wherein $R^1$, $R^2$, $R^3$, $R^4$, R, ring A, ring B and Hal represent the same meaning as described above.

E represents a Si atom or a Ge atom).

When $Z^1$ and $Z^2$ are a group represented by the formula (Z-4), the compound represented by the formula (1) can be produced, for example, by reacting the above-described compound represented by the formula (s12) and a compound represented by the formula (s14) according to the Buchwald-Hartwig amination. The compound obtained in this case is a compound represented by the formula (s15).

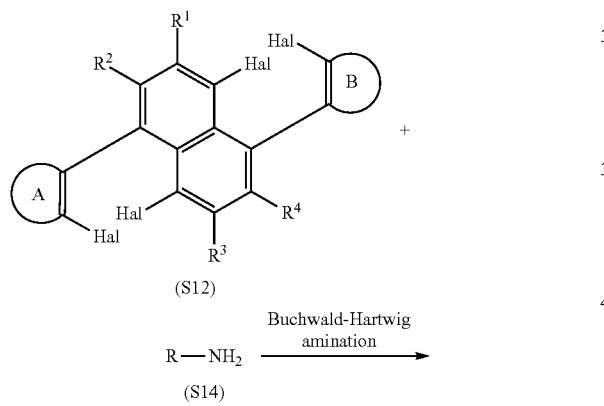

(wherein $R^1$, $R^2$, $R^3$, $R^4$, R, ring A, ring B and Hal represent the same meaning as described above.)

When $Z^1$ and $Z^2$ are a group represented by the formula (Z-6) to the formula (Z-11), the compound represented by the formula (1) can be produced, for example, by reacting a compound represented the formula (s16) and an oxidizing agent such as iron chloride and the like. The compound obtained in this case is a compound represented by the formula (s17).

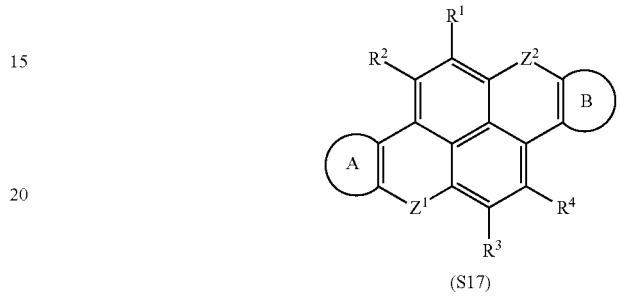

(S17)

(wherein $R^1$, $R^2$, $R^3$, $R^4$, ring A, ring B, $Z^1$ and $Z^2$ represent the same meaning as described above.)

<Polymer Compound>

(First Structural Unit)

The polymer compound of the present invention is a polymer compound having a structural unit represented by the formula (3) (hereinafter, referred to as "first structural unit" in some cases). The polymer compound of the present invention can be suitably produced by using the above-described compound represented by the formula (1) (may also be the above-described compound represented by the formula (2)) as a raw material. The first structural unit may be contained singly or two or more first structural units may be contained in the polymer compound. The polymer compound of the present invention is preferably a conjugated polymer compound.

(3)

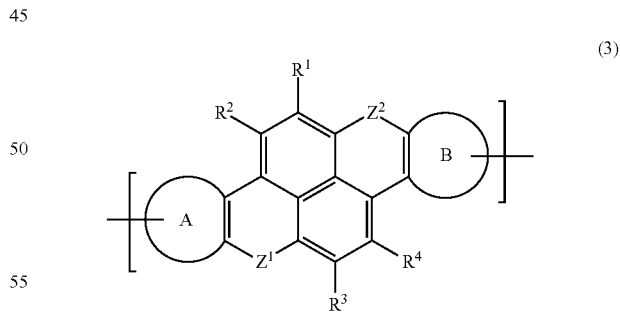

(wherein $R^1$, $R^2$, $R^3$, $R^4$, ring A, ring B, $Z^1$ and $Z^2$ represent the same meaning as described above.)

From the standpoint of easiness of synthesis of a compound as a raw material of the polymer compound of the present invention, the structural unit represented by the formula (3) is preferably a structural unit represented by the formula (4).

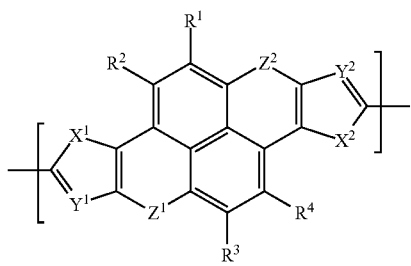

(wherein $R^1$, $R^2$, $R^3$, $R^4$, ring A, ring B, $X^1$, $X^2$, $Y^1$, $Y^2$, $Z^1$ and $Z^2$ represent the same meaning as described above.)

(4)

Preferable specific examples of the structural unit represented by the formula (3) include, for example, structural units represented by the following formula (3-1) to formula (3-31).

From the standpoint of further enhancing the electric field-effect mobility and the ON/OFF ratio of an organic transistor produced by using the compound of the present invention, compounds represented by the formula (3-1) to the formula (3-12) are preferable, compounds represented by the formula (3-1) to the formula (3-5) or the formula (3-7) to the formula (3-12) are more preferable, compounds represented by the formula (3-2) to the formula (3-5) or the formula (3-8) to the formula (3-10) are further preferable.

3-1
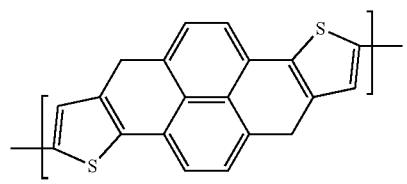

3-2
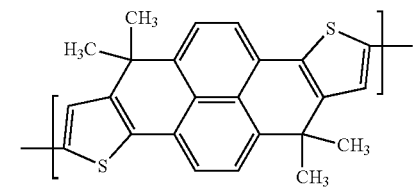

3-3
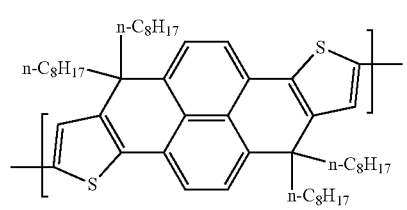

3-4
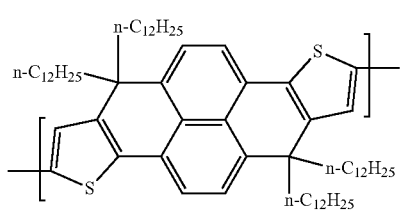

3-5
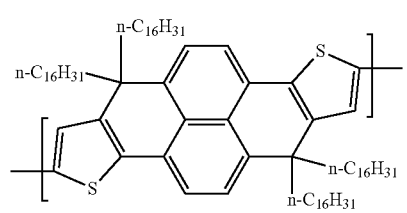

3-6
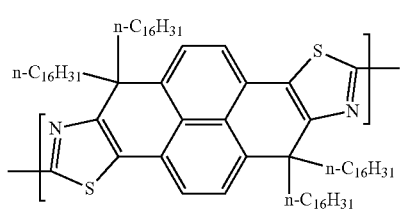

3-=7
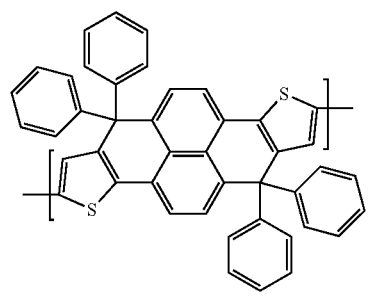

3-8
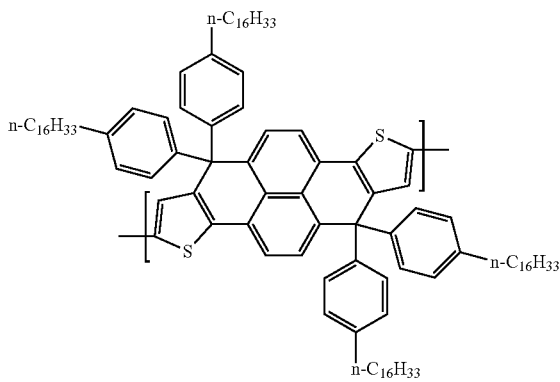

-continued
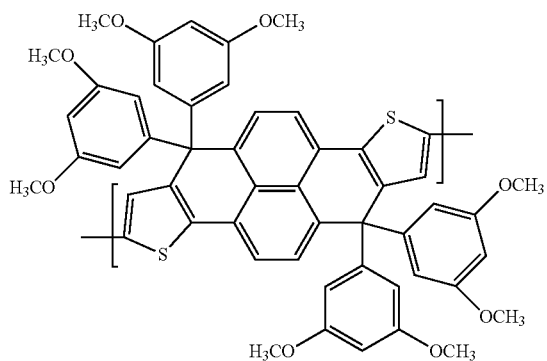
3-9
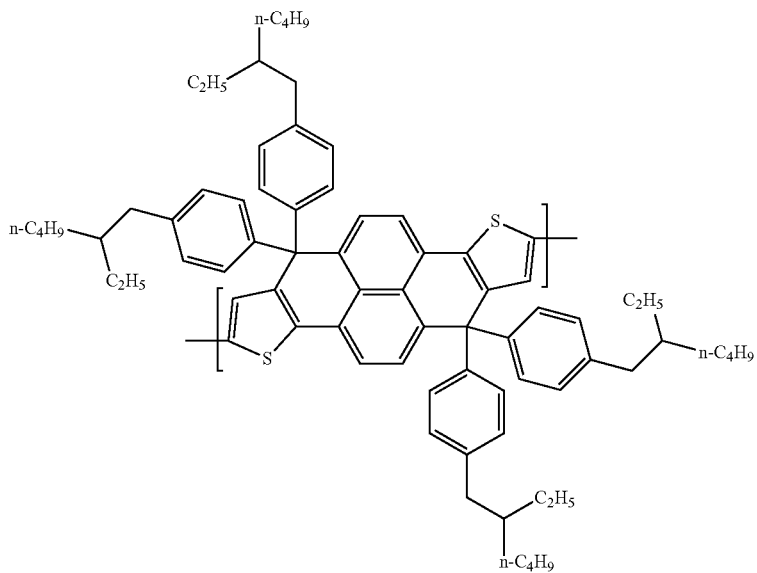
3-10
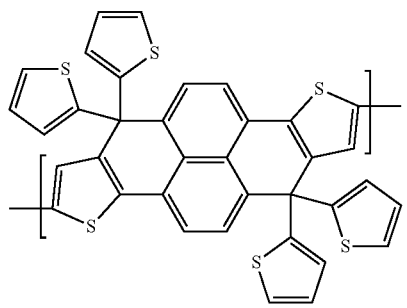
3-11
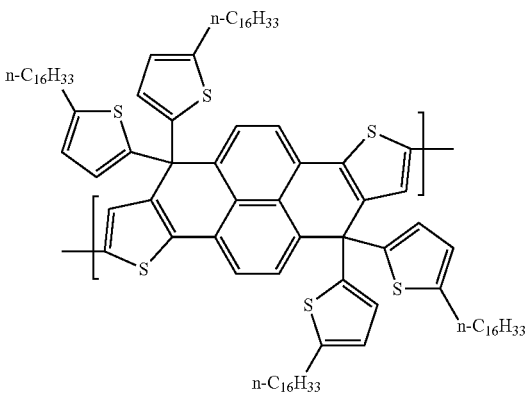
3-12
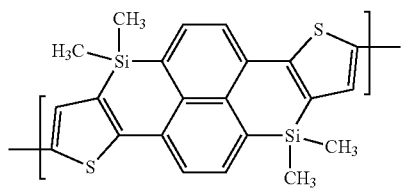
3-13
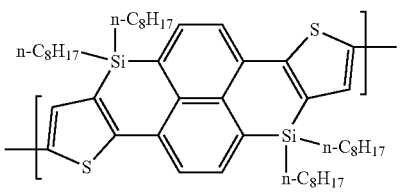
3-14

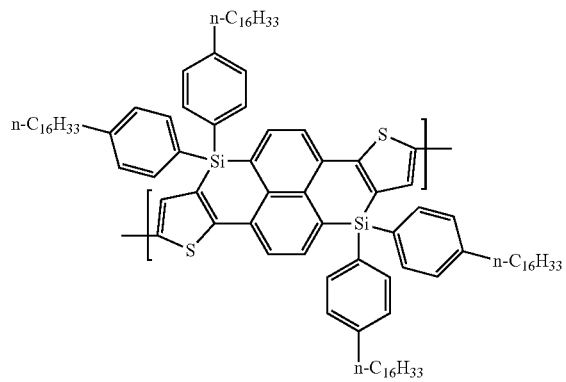
3-15
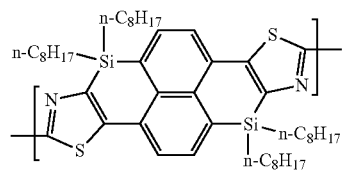
3-16
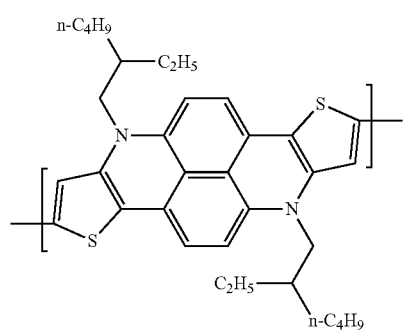
3-17
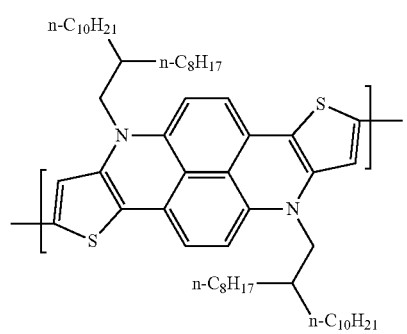
3-18
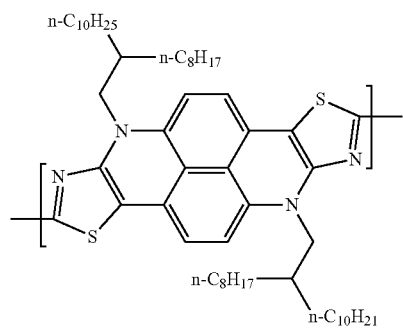
3-19
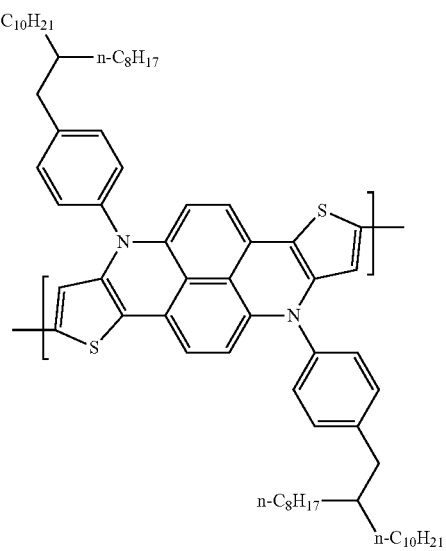
3-20

-continued
3-21
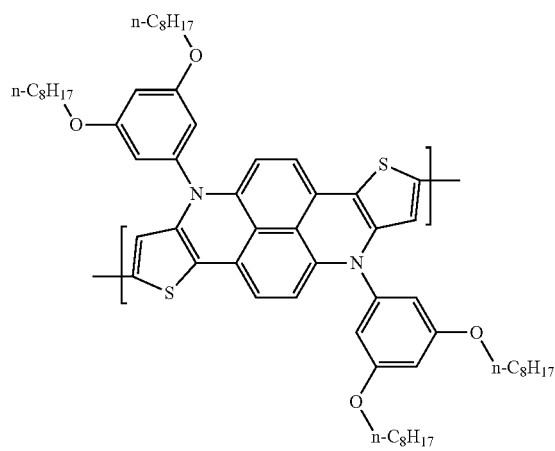
3-22
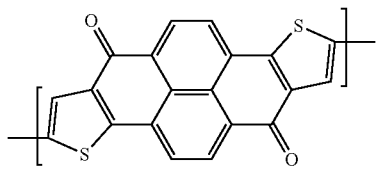
3-23
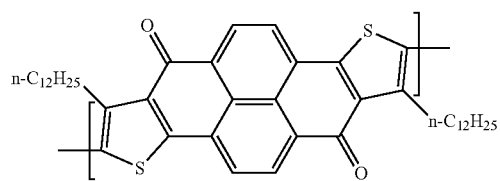
3-24
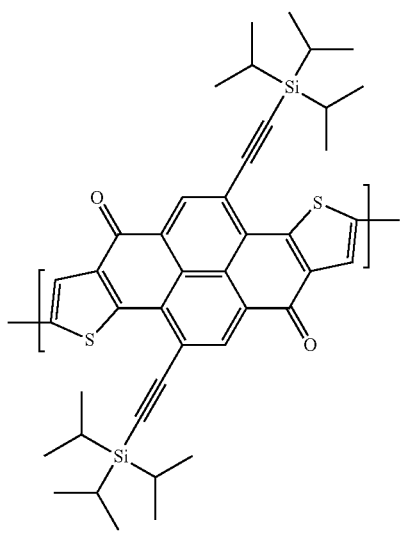
3-25
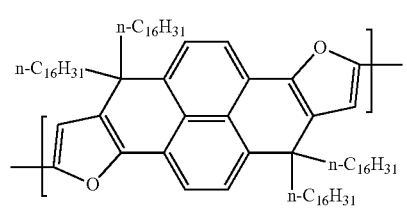
3-26
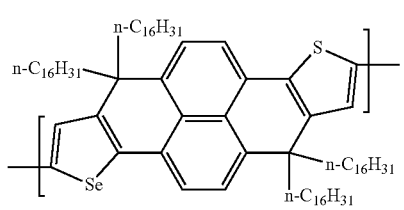
3-27
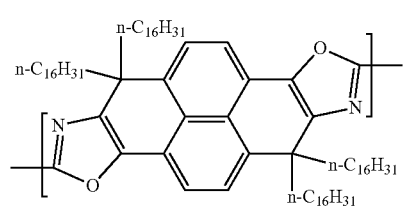
3-28
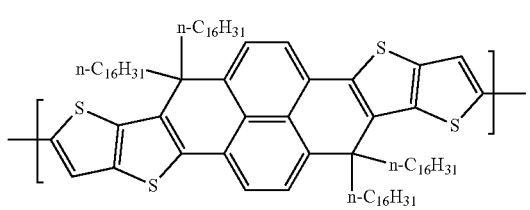
3-29
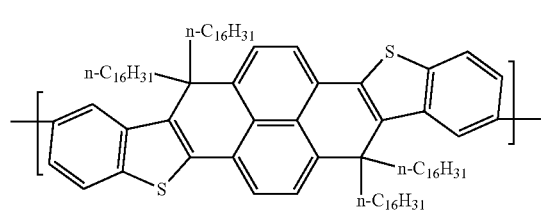
3-30
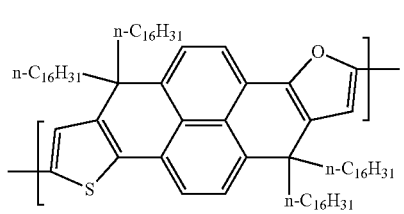

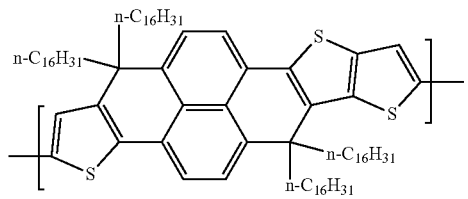

(Second Structural Unit)

It is preferable that the polymer compound of this embodiment contains further a structural unit represented by the formula (5) (hereinafter, referred to as "second structural unit" in some cases), in addition to the above-described structural unit represented by the formula (3).

(5)

(wherein Ar represents an arylene group or a di-valent heterocyclic group, and these groups may have a substituent. Here, Ar is different from the structural unit represented by the formula (3).).

When the second structural unit is contained, it is preferable that a structural unit represented by the formula (3) (may also be a structural unit represented by the formula (4)) and a structural unit represented by the formula (5) form conjugation.

In the present specification, conjugation denotes a state in which an unsaturated bond-a single bond-an unsaturated bond are chained in this order, two π bonds in the π orbital are adjacent, respective π electrons are disposed parallel, and π electrons are not localized on an unsaturated bond but π electrons spread onto an adjacent single bond and π electrons are delocalized. Here, the unsaturated bond denotes a double bond or a triple bond.

The arylene group is an atomic group remaining after removing, from an aromatic hydrocarbon, two hydrogen atoms bonded directly to carbon atoms constituting the ring, and the number of carbon atoms of the aromatic hydrocarbon is usually 6 to 60, preferably 6 to 20. The above-described number of carbon atoms does not include the number of carbon atoms of a substituent.

The arylene group includes a group having a benzene ring, a group having a condensed ring, a group obtained by directly bonding two or more rings selected from the group consisting of independent benzene rings and condensed rings, and a group obtained by bonding two or more rings selected from the group consisting of independent benzene rings and condensed rings via a group such as vinylene or the like.

As the arylene group, for example, arylene groups represented by the following formulae 1 to 12 are exemplified.

3-31

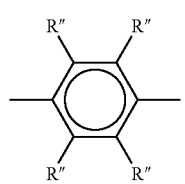
1

-continued

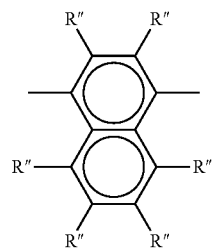
2

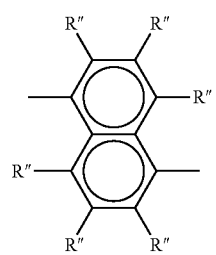
3

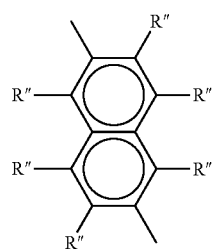
4

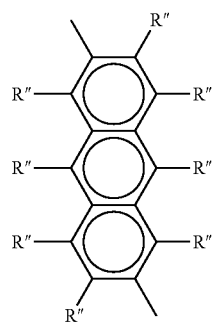
5

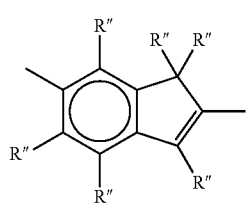
6

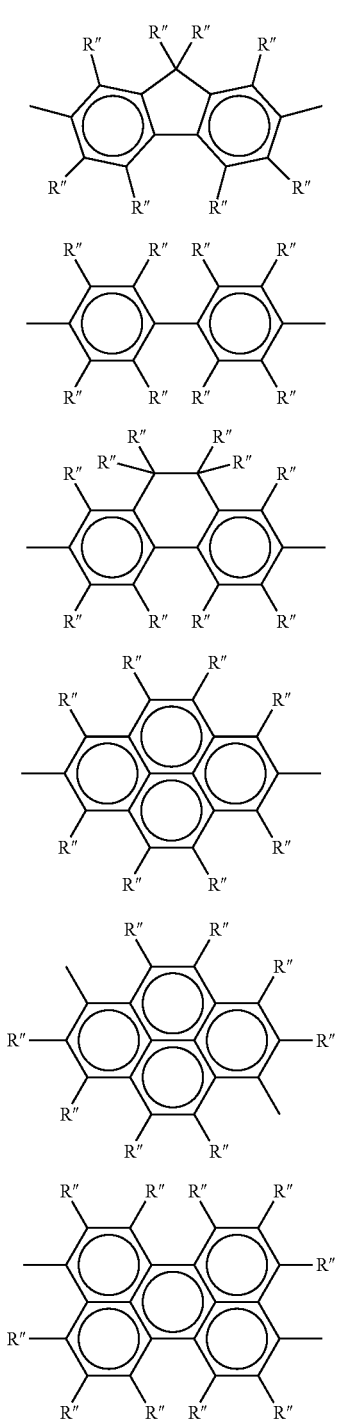

(wherein R″ represents a hydrogen atom, an alkyl group, an alkoxy group, an alkylthio group, an aryl group, a mono-valent heterocyclic group or a halogen atom. A plurality of R″ may be the same or different.)

The definitions and specific examples of the alkyl group, alkoxy group, alkylthio group, aryl group, mono-valent heterocyclic group or halogen atom represented by R″ are the same as the definitions and specific examples of the above-described alkyl group, alkoxy group, alkylthio group, aryl group, mono-valent heterocyclic group or halogen atom represented by $R^1$.

The di-valent heterocyclic group is an atomic group remaining after removing, from a heterocyclic compound, two hydrogen atoms bonded directly to carbon atoms constituting the ring. The number of carbon atoms of the heterocyclic compound is usually 2 to 30, preferably 3 to 20. The above-described number of carbon atoms does not include the number of carbon atoms of a substituent. The di-valent heterocyclic group is preferably a di-valent aromatic heterocyclic ring group.

Here, the heterocyclic compound includes organic compounds having a cyclic structure in which elements constituting the ring include not only a carbon atom but also a hetero atom such as an oxygen atom, a sulfur atom, a selenium atom, a nitrogen atom, a phosphorus atom, a boron atom, an arsenic atom and the like contained in the ring.

The di-valent heterocyclic group includes a group having a condensed ring, and a group obtained by directly bonding two or more rings selected from the group consisting of independent heterocyclic rings and condensed rings.

As the di-valent heterocyclic group, for example, di-valent heterocyclic groups represented by the following formulae 13 to 63 are exemplified.

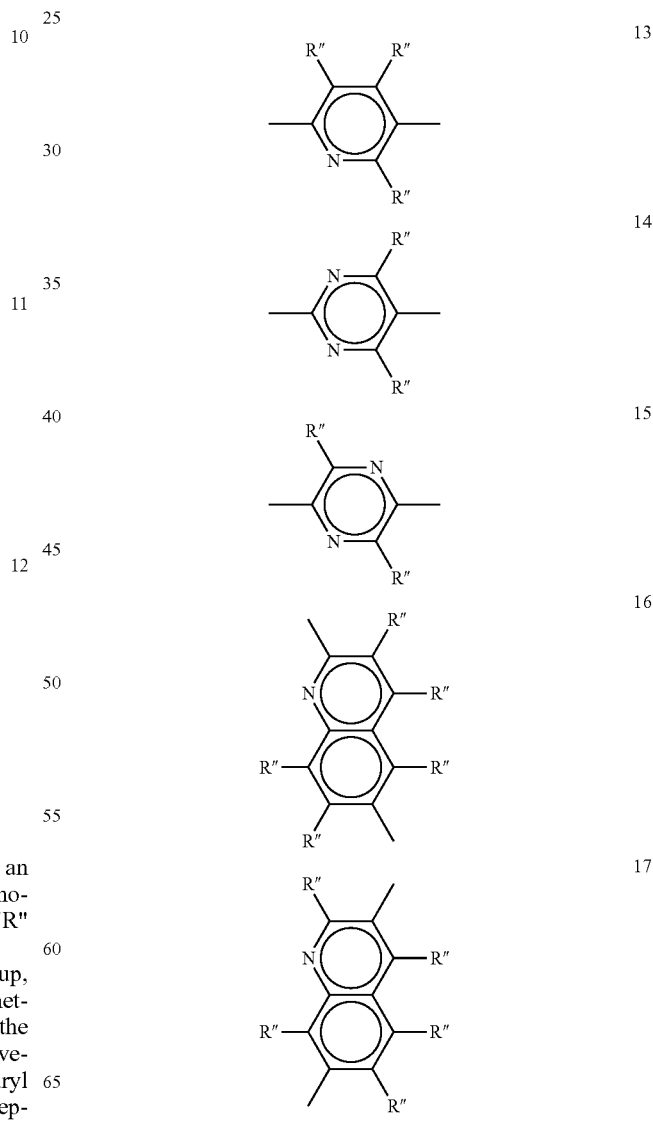

-continued
18
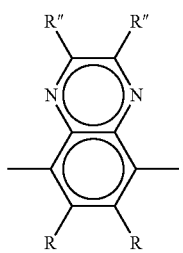
19
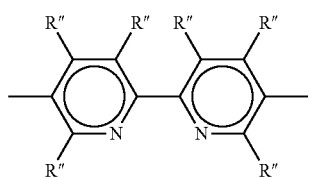
20
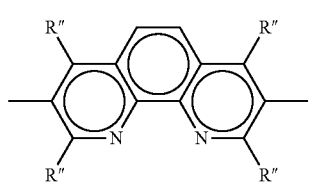
21
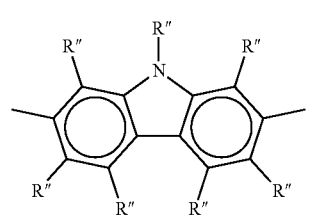
22
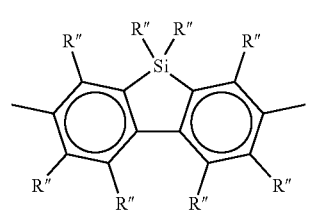
23
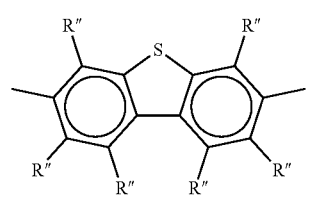
24
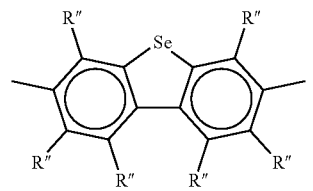
25
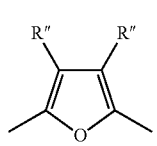
-continued
26
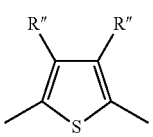
27
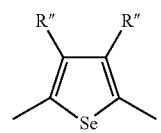
28
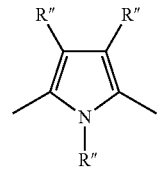
29
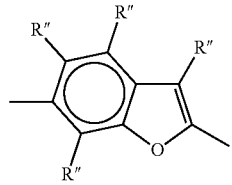
30
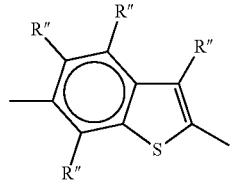
31
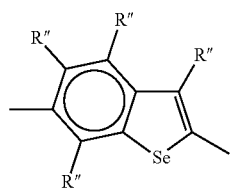
32
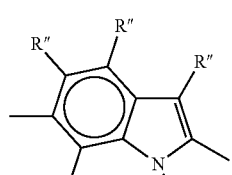
33
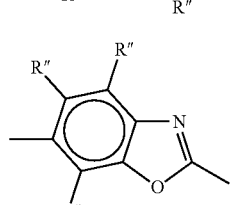
34
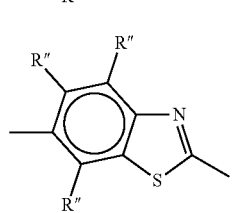

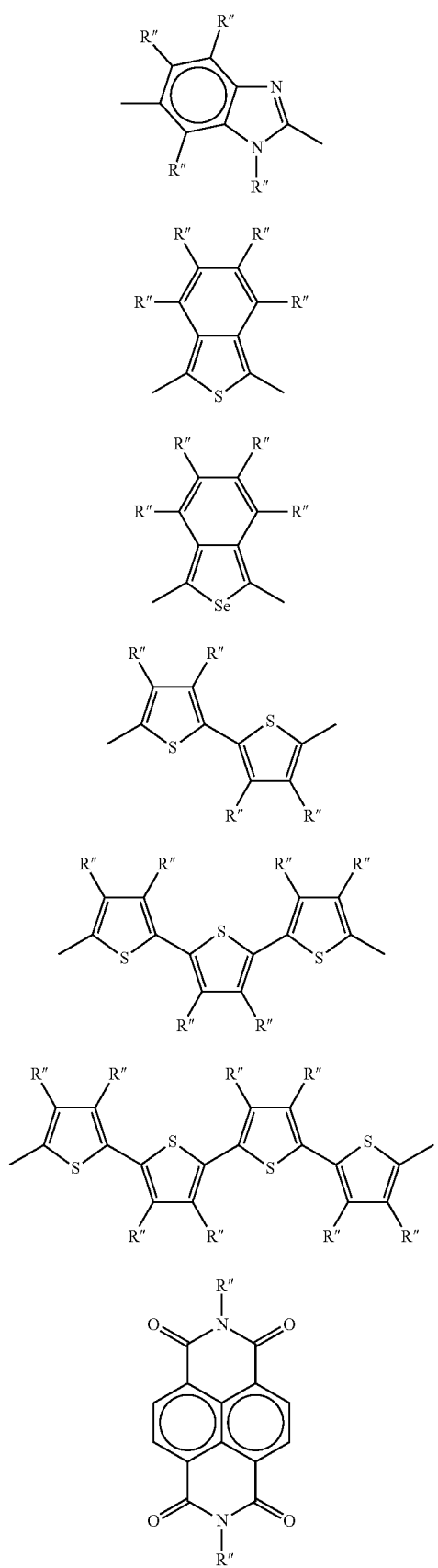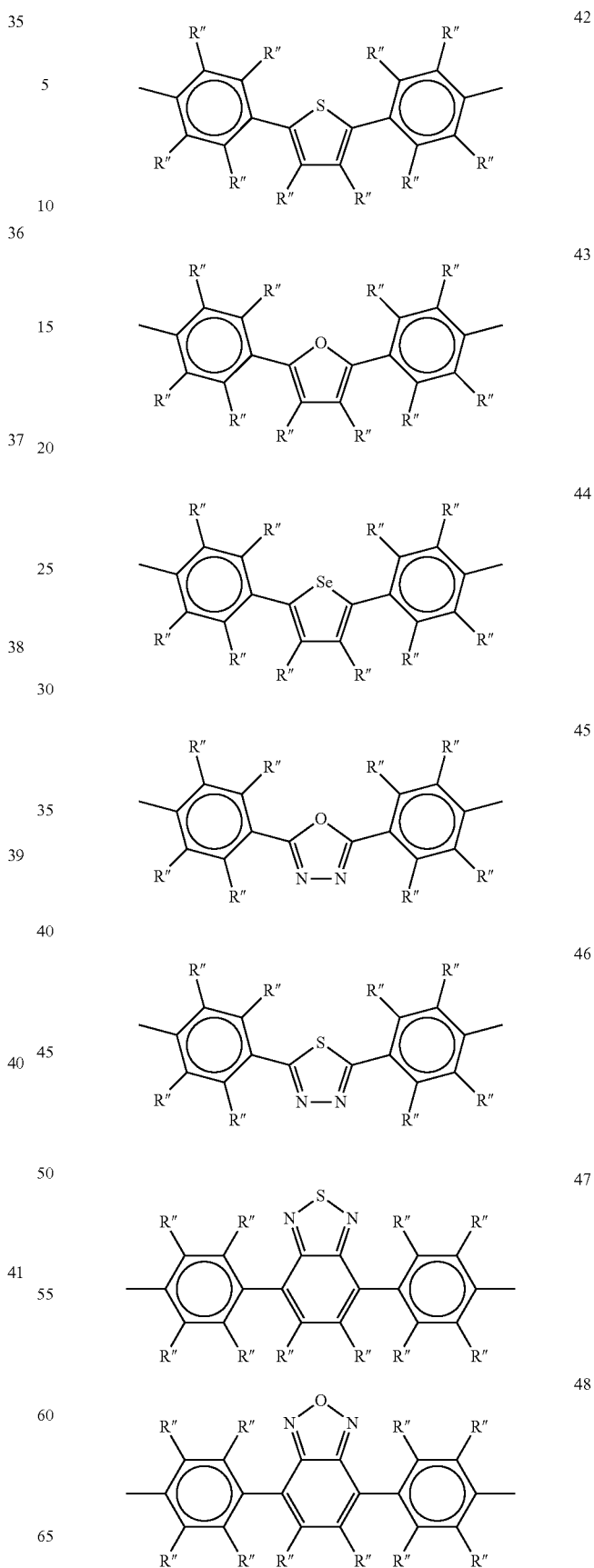

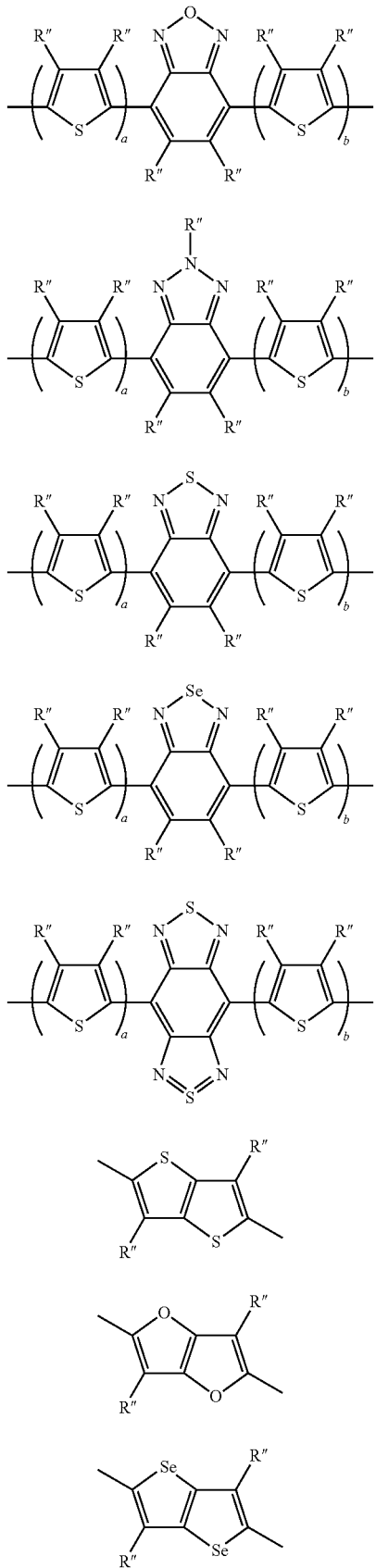
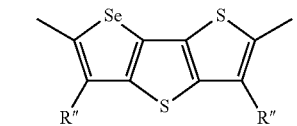
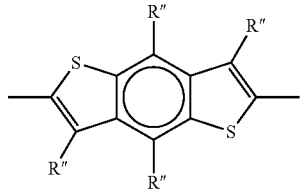
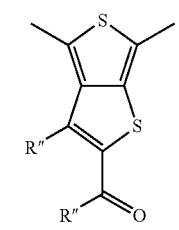
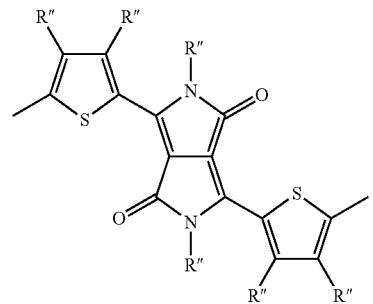
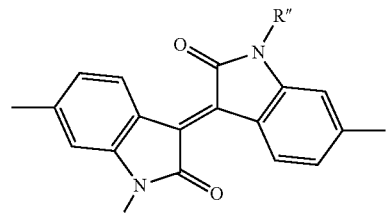
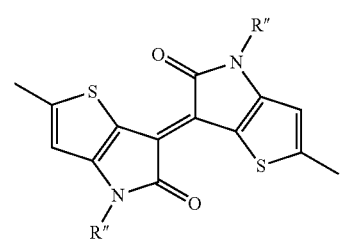
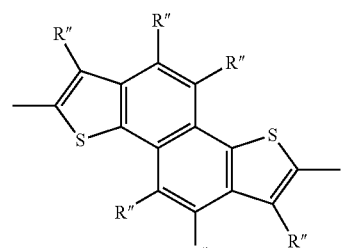
(wherein R″ represents the same meaning as described above.

a and b represent each independently the repetition number, and usually an integer of 0 to 5, preferably an integer of 0 to 3, more preferably an integer of 0 to 1.).

From the standpoint of further enhancing the electric field-effect mobility and the ON/OFF ratio of an organic transistor produced by using the polymer compound of this embodiment, the second structural unit is preferably a di-valent heterocyclic group, more preferably a di-valent heterocyclic group represented by the formula 49 to the formula 53 or the formula 60, further preferably a di-valent heterocyclic group represented by the formula 51.

The polystyrene-equivalent number-average molecular weight (Mn) of the polymer compound of the present invention measured by gel permeation chromatography (hereinafter, referred to as "GPC") is usually $1 \times 10^3$ to $1 \times 10^7$. From the standpoint of formation of a thin film which is excellent in fabricating a thin film, the number-average molecular weight is preferably $3 \times 10^3$ or more. From the standpoint of enhancing solubility in a solvent and making thin film fabrication easy, the number-average molecular weight is preferably $1 \times 10^6$ or less.

The polymer compound of the present invention shows high solubility in a solvent (preferably, an organic solvent), and specifically, the polymer compound of the present invention preferably has solubility at which a solution containing the polymer compound of the present invention in an amount of 0.1 wt % or more can be produced, more preferably has solubility at which a solution containing the polymer compound in an amount of 0.4 wt % or more can be produced.

In the polymer compound of the present invention, it is permissible that at least one of the above-described structural unit represented by the formula (3) is contained in the polymer compound, and it is preferable that three or more structural units represented the formula (3) are contained in the polymer compound, it is further preferable that five or more structural units represented the formula (3) are contained in the polymer compound.

The polymer compound of the present invention may be any kind of copolymer, and for example, may be any of a block copolymer, a random copolymer, an alternative copolymer, a graft copolymer and the like. From the standpoint of further enhancing the electric field-effect mobility and the ON/OFF ratio of an organic transistor produced by using the polymer compound of this embodiment, the polymer compound of the present invention is preferably a copolymer of a structural unit represented by the formula (3) and a structural unit represented by the formula (5), more preferably an alternative copolymer of a structural unit represented by the formula (3) and a structural unit represented by the formula (5).

If a group active against the polymerization reaction remains on the end of a molecular chain of the polymer compound of the present invention, the electric field-effect mobility of an organic transistor produced by using the polymer compound possibility lowers. Thus, it is preferable that the molecular chain end is composed of a stable group such as an aryl group, a mono-valent aromatic heterocyclic group and the like.

<Method of Producing Polymer Compound>

Next, the method of producing the polymer compound of the present invention will be explained.

The polymer compound of the present invention may be produced by any method, and for example, can be synthesized by a known polymerization method such as aryl coupling and the like using a suitable catalyst from a compound represented by the formula: $X^{11}$-$A^{11}$-$X^{12}$ and a compound represented by the formula: $X^{13}$-$A^{12}$-$X^{14}$ wherein if necessary the compounds are dissolved in an organic solvent and if necessary a base is added therein.

In the above-described formula, $A^{11}$ represents a structural unit represented by the formula (3) and $A^{12}$ represents a structural unit represented by the formula (5). $X^{11}$, $X^{12}$, $X^{13}$ and $X^{14}$ represent each independently a polymerization reactive group.

The polymerization reactive group includes a halogen atom, a borate residue, a boric acid residue (—B(OH)$_2$), a stannyl group substituted with three alkyl groups, and the like.

The halogen atom as the polymerization reactive group includes a fluorine atom, a chlorine atom, a bromine atom and an iodine atom.

The borate residue as the polymerization reactive group includes groups represented by the following formulae.

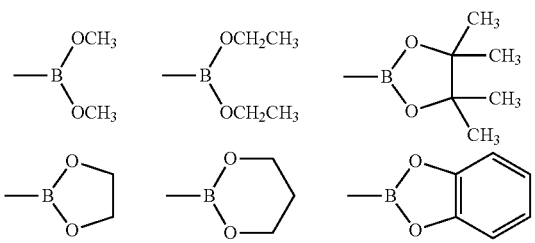

The stannyl group substituted with three alkyl groups as the polymerization reactive group includes a stannyl group substituted with three methyl groups and a stannyl group substituted with three butyl groups.

The above-described polymerization method such as aryl coupling and the like includes a method of polymerization according to the Suzuki coupling reaction (Chemical Review, 1995, vol. 95, pp. 2457-2483), a method of polymerization according to the Stille coupling reaction (European Polymer Journal, 2005, vol. 41, pp. 2923-2933), and the like.

The polymerization reactive group is a halogen atom, a borate residue, a boric acid residue or the like in the case of use of a nickel catalyst or a palladium catalyst such as in the Suzuki coupling reaction and the like. From the standpoint of simplicity of the polymerization reaction, a bromine atom, an iodine atom and a borate residue are preferable.

When the polymer compound of the present invention is polymerized by the Suzuki coupling reaction, the ratio of the total mol number of the bromine atom and the iodine atom as the polymerization reactive group to the total mol number of the borate residue as the polymerization reactive group is preferably 0.7 to 1.3, more preferably 0.8 to 1.2.

The polymerization reactive group is a halogen atom, a stannyl group substituted with three alkyl groups or the like in the case of use of a palladium catalyst such as in the Stille coupling reaction and the like. From the standpoint of simplicity of the polymerization reaction, a bromine atom, an iodine atom and a stannyl group substituted with three alkyl groups are preferable.

When the polymer compound of the present invention is polymerized by the Stille coupling reaction, the ratio of the total mol number of the bromine atom and the iodine atom as the polymerization reactive group to the total mol number of the stannyl group substituted with three alkyl groups as the polymerization reactive group is preferably 0.7 to 1.3, more preferably 0.8 to 1.2.

The organic solvent used for polymerization includes benzene, toluene, xylene, chlorobenzene, dichlorobenzene, tetrahydrofuran, dioxane and the like. These organic solvents may be used singly or two or more of them may be used in combination.

The base used for polymerization includes inorganic bases such as sodium carbonate, potassium carbonate, cesium carbonate, potassium fluoride, cesium fluoride, tripotassium phosphate and the like, and organic bases such as tetrabutylammonium fluoride, tetrabutylammonium chloride, tetrabutylammonium bromide, tetraethylammonium hydroxide, tetrabutylammonium hydroxide and the like.

The catalyst used for polymerization is a catalyst composed of a transition metal complex such as a palladium complex such as tetrakis(triphenylphosphine)palladium, tris(dibenzylideneacetone)dipalladium, palladium acetate, dichlorobistriphenylphosphinepalladium and the like, and, if necessary, composed of a ligand such as triphenylphosphine, tri-tert-butylphosphine, tricyclohexylphosphine and the like. As the catalyst, those synthesized previously may be used or those prepared in the reaction system may be used as they are. These catalysts may be used singly or two or more of them may be used in combination.

The reaction temperature of the polymerization is preferably 0 to 200° C., more preferably 0 to 150° C., further preferably 0 to 120° C.

The reaction time of the polymerization is usually 1 hour or more, preferably 2 to 500 hours.

The post treatment of the polymerization can be conducted by a known method, and for example, the reaction solution obtained in the above-described polymerization can be added to a lower alcohol such as methanol and the like to cause deposition of a precipitate which is then filtrated and dried.

When the purity of the polymer compound of the present invention is low, it is preferable that the compound is purified by a method such as re-crystallization, continuous extraction with a Soxhlet extractor, column chromatography and the like.

<Organic Semiconductor Material>

The organic semiconductor material of the present invention may be one containing the compound of the present invention (may also be the polymer compound of the present invention) singly, or one containing two or more of them. The organic semiconductor material of this embodiment may further contain a compound having carrier transportability (may be a low molecular weight compound or a high molecular weight compound), in addition to the compound of the present invention. When the organic semiconductor material of this embodiment contains a component other than the compound of the present invention, the compound of the present invention is contained in an amount of preferably 30 wt % or more, more preferably 50 wt % or more, further preferably 70 wt % or more.

The compound having carrier transportability includes low molecular weight compounds such as arylamine derivatives, stilbene derivatives, oligothiophene and derivatives thereof, oxadiazole derivatives, fullerenes and derivatives thereof and the like, and, polyvinylcarbazole and derivatives thereof, polyaniline and derivatives thereof, polythiophene and derivatives thereof, polypyrrole and derivatives thereof, polyphenylenevinylene and derivatives thereof, polythienylenevinylene and derivatives thereof, polyfluorene and derivatives thereof and the like.

The organic semiconductor material may contain as a polymer binder a different polymer compound material from the polymer compound of the present invention, for enhancing its property. As the polymer binder, those not excessively lowering carrier transportability are preferable.

Examples of the polymer binder include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride and polysiloxane.

<Organic Semiconductor Device>

Since the compound of the present invention and the polymer compound of the present invention have high mobility, when an organic thin film containing the compound of the present invention (preferably the polymer compound of the present invention) is used in an organic semiconductor device, electrons and holes injected from an electrode and charges generated by light absorption can be transported. Utilizing these properties, the compound of the present invention can be suitably used in various organic semiconductor devices such as a photoelectric conversion device, an organic transistor, an organic electroluminescent device and the like. These devices will be illustrated individually, below.

(Photoelectric Conversion Device)

The photoelectric conversion device containing the compound of the present invention (preferably, the polymer compound of the present invention) has at least one active layer containing the compound of the present invention between a pair of electrodes at least one of which is transparent or semi-transparent.

A preferable embodiment of the photoelectric conversion device containing the compound of the present invention has a pair of electrodes at least one of which is transparent or semi-transparent, and an active layer formed of a composition of a p-type organic semiconductor and an n-type organic semiconductor. It is preferable that the compound of the present invention is used as a p-type organic semiconductor. The action mechanism of the photoelectric conversion device of this configuration will be explained. The energy of incident light from a transparent or semi-transparent electrode is absorbed by an electron accepting compound such as fullerene derivatives and the like (n-type organic semiconductor) and/or an electron donating compound such as the compound of the present invention and the like (p-type organic semiconductor), to generate an exciton composed of bound electrons and holes. If the generated exciton transfers and reaches the heterojunction interface at which an electron accepting compound and an electron donating compound are adjacent, electrons and holes separate owing to a difference of respective HOMO energy and LUMO energy at the surface, and independently movable charges (electrons and holes) are generated. The generated charges transfer to respective electrodes, and can be taken out outward as electric energy (current).

The photoelectric conversion device produced by using the compound of the present invention (preferably, the polymer compound of the present invention) is formed usually on a substrate. This substrate is advantageously one which does not chemically change in forming an electrode and forming a layer of an organic material. The material of the substrate includes, for example, glass, plastics, polymer films and silicon. In the case of an opaque substrate, it is preferable that the opposite electrode (namely, an electrode far from the substrate) is transparent or semi-transparent.

Another embodiment of the photoelectric conversion device having the compound of the present invention (preferably, the polymer compound of the present invention) is a photoelectric conversion device containing a first active layer containing the compound of the present invention and a second active layer containing an electron accepting compound such as fullerene derivatives and the like adjacent to the first active layer, between a pair of electrodes at least one of which is transparent or semi-transparent.

The above-described transparent or semi-transparent electrode material includes an electrically conductive metal oxide film, a semi-transparent metal thin film and the like. Specifically, use is made of a film fabricated by using an electrically conductive material composed of indium oxide, zinc oxide, tin oxide, and a composite thereof: indium.tin.oxide (hereinafter, referred to as "ITO" in some cases), indium.zinc.oxide and the like; NESA and, gold, platinum, silver, copper and the like, and preferable are ITO, indium.zinc.oxide and tin oxide. The method of fabricating the electrode includes a vacuum vapor deposition method, a sputtering method, an ion plating method, a plating method and the like. Further, transparent electrically conductive films of organic materials such as polyaniline and derivatives thereof, polythiophene and derivatives thereof and the like may also be used as the electrode material.

One electrode may not be transparent, and as the electrode material, metals, electrically conductive polymers and the like can be used. Specific examples of the electrode material include metals such as lithium, sodium, potassium, rubidium, cesium, magnesium, calcium, strontium, barium, aluminum, scandium, vanadium, zinc, yttrium, indium, cerium, samarium, europium, terbium, ytterbium and the like, and alloys composed of two or more of them, or alloys composed of at least one of the above-described metals and at least one selected from the group consisting of gold, silver, platinum, copper, manganese, titanium, cobalt, nickel, tungsten and tin; graphite, graphite intercalation compounds, polyaniline and derivatives thereof and polythiophene and derivatives thereof. The alloy includes a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy and the like.

An additive intermediate layer other than the active layer may be used as means for improving photoelectric conversion efficiency. The material used in the intermediate layer includes halides of alkali metals and alkaline earth metals such as lithium fluoride and the like, oxides such as titanium oxide and the like, PEDOT (poly-3,4-ethylenedioxythiophene) and the like.

The active layer may contain the compound of the present invention (preferably, the polymer compound of the present invention) singly or two or more of them in combination. Further, a compound other than the compound of the present invention can be mixed and used as an electron donating compound and/or an electron accepting compound in the active layer. The electron donating compound and the electron accepting compound are determined relatively according to the energy level of these compounds.

The above-described electron donating compound includes, for example, pyrazoline derivatives, arylamine derivatives, stilbene derivatives, triphenyldiamine derivatives, oligothiophene and derivatives thereof, polyvinylcarbazole and derivatives thereof, polysilane and derivatives thereof, polysiloxane derivatives having an aromatic amine residue in the side chain or main chain, polyaniline and derivatives thereof, polythiophene and derivatives thereof, polypyrrole and derivatives thereof, polyphenylenevinylene and derivatives thereof, and polythienylenevinylene and derivatives thereof, in addition to the compound of the present invention (preferably, the polymer compound of the present invention).

The above-described electron accepting compound includes, for example, carbon materials, metal oxides such as titanium oxide and the like, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, phenanthrene derivatives such as 2,9-dimethyl-4,7-diphenyl-1,10-phenanthroline (basocuproin) and the like, fullerene and fullerene derivatives, in addition to the compound of the present invention (preferably, the polymer compound of the present invention), and preferable are titanium oxide, carbon nanotube, fullerene and fullerene derivatives, particularly preferable are fullerene and fullerene derivatives.

The fullerene and fullerene derivatives include $C_{60}$, $C_{70}$, $C_{76}$, $C_{78}$, $C_{84}$ and derivatives thereof. Specific structures of derivatives of fullerene include those as described below.

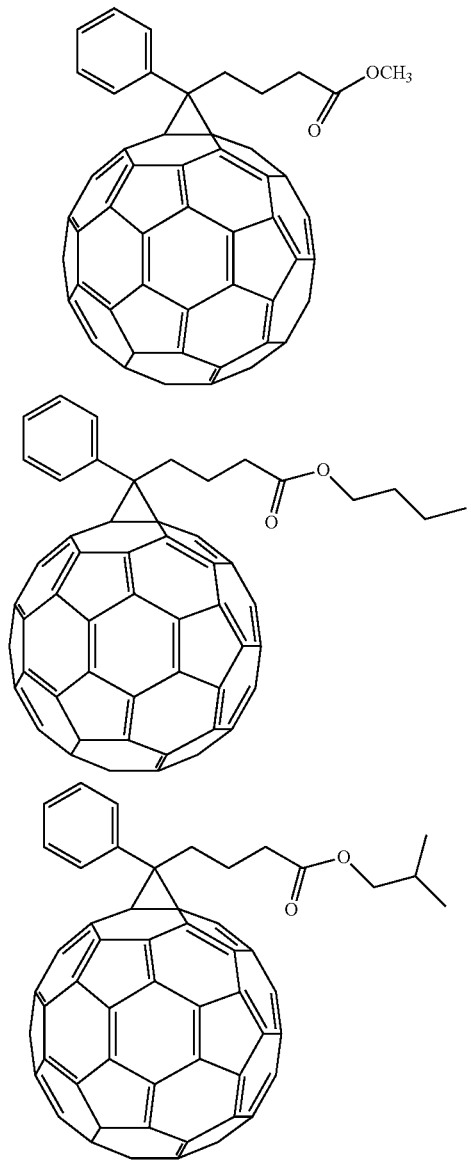

57
-continued
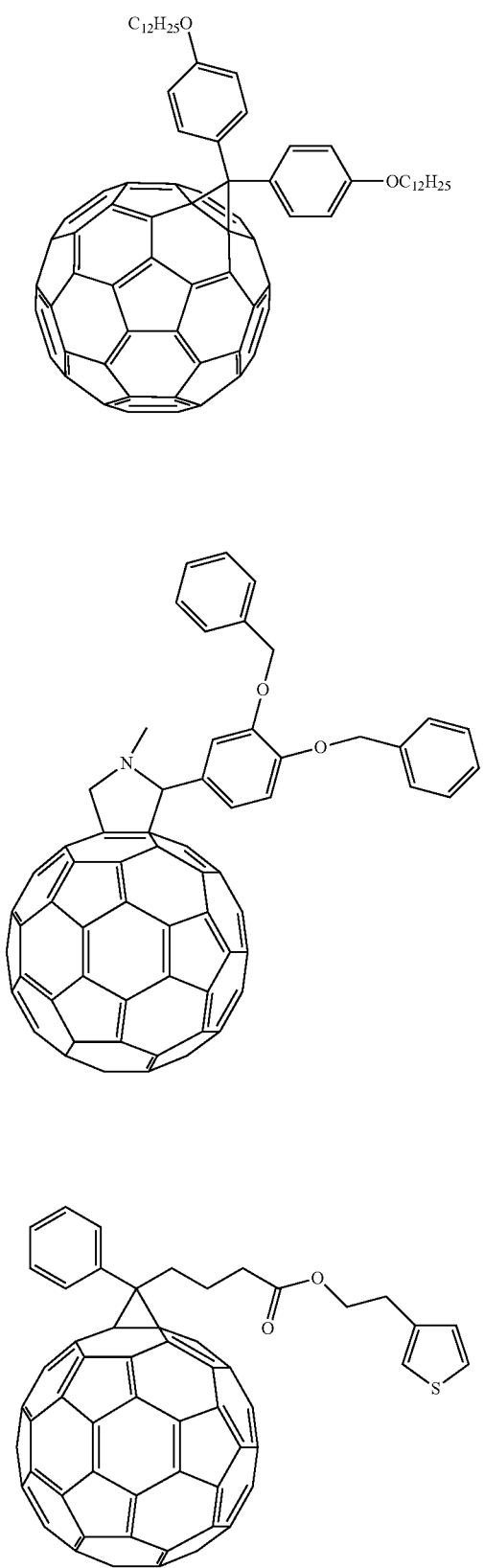
58
-continued
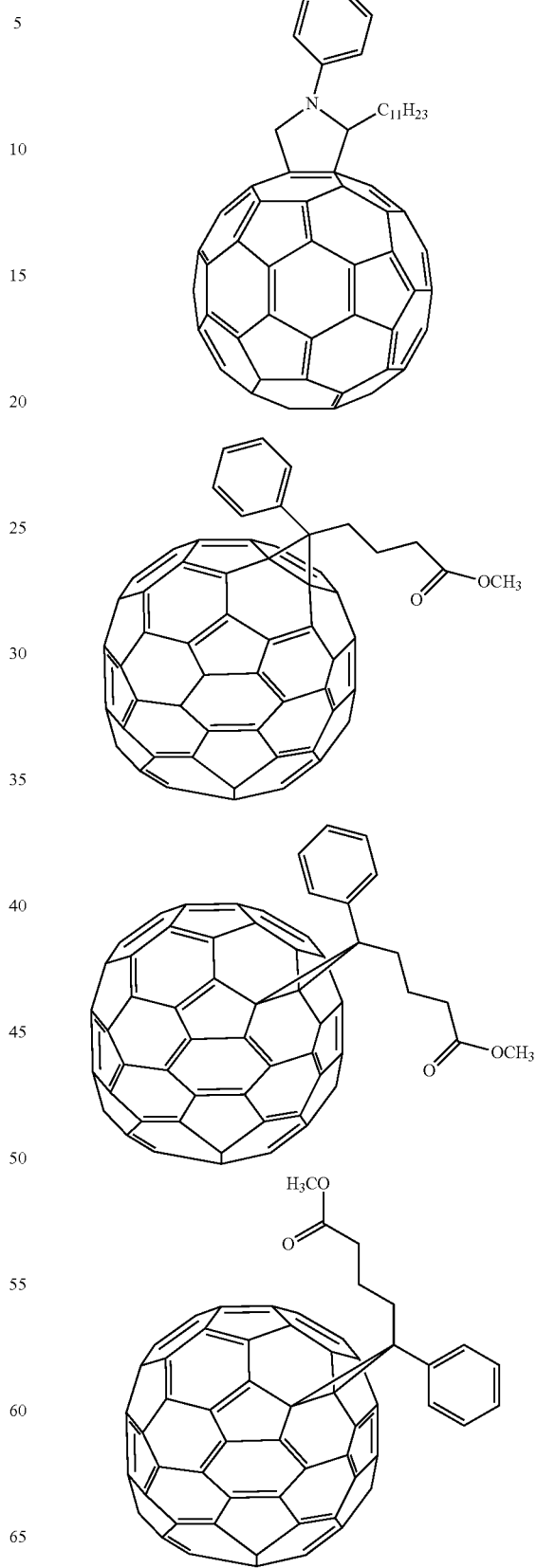

Examples of fullerene derivatives include methyl [6,6] phenyl C61 butyrate (C60PCBM, [6,6]-Phenyl C61 butyric acid methyl ester), methyl [6,6] phenyl C70 butyrate (C70PCBM, [6,6]-Phenyl C70 butyric acid methyl ester), methyl [6,6] phenyl C84 butyrate (C84PCBM, [6,6]-Phenyl C84 butyric acid methyl ester), methyl [6,6] thienyl C60 butyrate ([6,6]-Thienyl C60 butyric acid methyl ester), and the like.

When the active layer contains the compound of the present invention (preferably, the polymer compound of the present invention) and a fullerene derivative, the proportion of the fullerene derivative is preferably 10 to 1000 parts by weight, more preferably 20 to 500 parts by weight with respect to 100 parts by weight of the compound of the present invention.

Usually, the thickness of the active layer is preferably 1 nm to 100 μm, more preferably 2 nm to 1000 nm, further preferably 5 nm to 500 nm, more preferably 20 nm to 200 nm.

The active layer may be produced by any method, and the production method includes, for example, a method of film formation from a solution containing the compound of the present invention (preferably, the polymer compound of the present invention), a method of film formation by a vacuum vapor deposition method.

The preferable method of producing a photoelectric conversion device is a method of producing a photoelectric conversion device having a first electrode and a second electrode and having an active layer between the first electrode and the second electrode, the method having a step of coating a solution (ink) containing the compound of the present invention (preferably, the polymer compound of the present invention) and a solvent on the first electrode by a coating method, and a step of forming the second electrode on the active layer.

The solvent used for film formation from a solution may be one which dissolves the compound of the present invention (preferably, the polymer compound of the present invention). The solvent includes, for example, unsaturated hydrocarbon solvents such as toluene, xylene, mesitylene, tetralin, decalin, bicyclohexyl, n-butylbenzene, sec-butylbenzene, tert-butylbenzene and the like, halogenated saturated hydrocarbon solvents such as such as carbon tetrachloride, chloroform, dichloromethane, dichloroethane, chlorobutane, bromobutane, chloropentane, bromopentane, chlorohexane, bromohexane, chlorocyclohexane, bromocyclohexane and the like, halogenated unsaturated hydrocarbon solvents such as chlorobenzene, dichlorobenzene, trichlorobenzene and the like, and ether solvents such as tetrahydrofuran, tetrahydropyran and the like. The compound of the present invention (particularly, the polymer compound of the present invention) can be dissolved in the above-described solvent usually in an amount of 0.1 wt % or more.

In the case of film formation using a solution, use can be made of coating methods such as a slit coat method, a knife coat method, a spin coat method, a casting method, a micro gravure coat method, a gravure coat method, a bar coat method, a roll coat method, a wire bar coat method, a dip coat method, a spray coat method, a screen printing method, a gravure printing method, a flexo printing method, an offset printing method, an inkjet printing method, a dispenser printing method, a nozzle coat method, a capillary coat method and the like, and preferable are a slit coat method, a capillary coat method, a gravure coat method, a micro gravure coat method, a bar coat method, a knife coat method, a nozzle coat method, an inkjet printing method and a spin coat method.

From the standpoint of film formability, the surface tension of a solvent at 25° C. is preferably larger than 15 mN/m, more preferably larger than 15 mN/m and smaller than 100 mN/m, further preferably lamer than 25 mN/m and smaller than 60 mN/m.

(Organic Thin Film Solar Battery)

A photoelectric conversion device using the compound of the present invention (preferably, the polymer compound of the present invention) can be irradiated with light such as solar light or the like through a transparent or semi-transparent electrode to cause generation of photovoltaic power between electrodes, and can be operated as an organic thin film solar battery. It is also possible that several organic thin film solar batteries are integrated and used as an organic thin film solar battery module.

Further, by irradiation with light through a transparent or semi-transparent electrode under the state of application of voltage between electrodes or under the state of no application of voltage, photocurrent flows, and operation as an organic optical sensor is possible. It is also possible that several organic optical sensors are integrated and used as an organic image sensor.

The organic thin film solar battery can adopt basically the same module structure as that of a conventional solar battery module. The solar battery module generally takes a structure in which cells are constituted on a supporting substrate made of a metal, ceramic and the like, its upper surface is covered with a filling resin, protective glass and the like and light is incorporated from the opposite side of the supporting substrate, however, can also take a structure in which a transparent material such as reinforced glass and the like is used for a supporting substrate, cells are constituted thereon and light is incorporated from the side of the transparent supporting substrate. Specifically, module structures called a super straight type, a sub straight type or a potting type, substrate-integrated module structures used in an amorphous silicon solar battery, and the like, are known. Also an organic thin film solar battery produced by using the polymer compound of the present invention can appropriately select these module structures depending on the use object and use place and environments.

Typical super straight type or sub straight type modules have a structure in which cells are placed at a prescribed interval between supporting substrates one or both of which are transparent and having undergone an anti-reflection treatment, adjacent cells are mutually connected via metal leads or flexible wiring and the like, a collection electrode is disposed on the outer edge, and the generated electric power is taken out outward. Between the substrates and the cells, various kinds of plastic materials such as ethylene vinyl acetate (EVA) and the like may be used in the form of a film or a filling resin depending on the object, for protection of the cells and for improvement of current collecting efficiency. In the case of use in a place wherein the surface is not required to be coated with a hard material such as a place receiving little impact from outside, it is possible that the surface protective layer is constituted of a transparent plastic film or the above-described filling resin is cured to give a protecting function, and one supporting substrate is deleted. The peripheral part of the supporting substrate is fixed in the form of a sandwich by metal flames for tight seal of the inside and for securing rigidity of the module, and a space between the supporting substrate and the flame is tightly sealed with a sealing material. If a flexible material is used for a cell itself or for a supporting substrate, a filling material and an insulation material, it is also possible to constitute a solar battery on a curved surface.

In the case of a solar battery using a flexible supporting body such as a polymer film and the like, cells are formed in series while conveying a roll-shaped supporting body, out into desired size, then, the peripheral part is sealed with a material which is flexible and having a moisture-proof property, thus a battery body can be fabricated. Further, a module structure called "SCAF" described in Solar Energy Materials and Solar Cells, 48, pp. 383-391 can also be adopted. Further, it is also possible that a solar battery using a flexible supporting body is adhered and fixed to curved glass or the like and used.

(Organic Electroluminescent Device)

The compound of the present invention (preferably, the polymer compound of the present invention) can also be used in an organic electroluminescent device (hereinafter, referred to as "organic EL device" in some cases). The organic EL device has a light emitting layer between a pair of electrodes at least one of which is transparent or semi-transparent. The organic EL device may contain a hole transporting layer and an electron transporting layer in addition to the light emitting layer. The compound of the present invention is contained in any of the light emitting layer, the hole transporting layer and the electron transporting layer. The light emitting layer may contain also a charge transporting material (generic name of an electron transporting material and a hole transporting material) in addition to the compound of the present invention. The organic EL device includes a device having an anode, a light emitting layer and a cathode, a device having an anode, a light emitting layer, an electron transporting layer and a cathode wherein the electron transporting layer containing an electron transporting material is disposed adjacent to the light emitting layer between the cathode and the light emitting layer, a device having an anode, a hole transporting layer, a light emitting layer and a cathode wherein the hole transporting layer containing a hole transporting material is disposed adjacent to the light emitting layer between the anode and the light emitting layer, a device having an anode, a hole transporting layer, a light emitting layer, an electron transporting layer and a cathode, and the like.

(Organic Transistor)

The organic transistor includes one having a constitution having a source electrode and a drain electrode, an active layer acting as a current pathway between these electrodes and containing the compound of the present invention (preferably, the polymer compound of the present invention), and a gate electrode controlling the amount of current passing through the current pathway. The organic transistor having such a constitution includes an electric field-effect type organic transistor, an electrostatic induction type organic transistor, and the like.

The electric field-effect type organic transistor is usually an organic transistor having a source electrode and a drain electrode, an active layer acting as a current pathway between these electrodes and containing the compound of the present invention (preferably, the polymer compound of the present invention), a gate electrode controlling the amount of current passing through the current pathway, and an insulation layer disposed between the active layer and the gate electrode. Particularly, preferable is an organic transistor in which a source electrode and a drain electrode are disposed adjacent to an active layer, further, a gate electrode is disposed sandwiching an insulation layer in contact with the active layer.

The electrostatic induction type organic transistor is usually an organic transistor having a source electrode and a drain electrode, an active layer acting as a current pathway between these electrodes and containing the compound of the present invention (preferably, the polymer compound of the present invention) and a gate electrode controlling the amount of current passing through the current pathway wherein the gate electrode is disposed in the active layer. Particularly, preferable is an organic transistor in which a source electrode, a drain electrode and the above-described gate electrode are disposed adjacent to the above-described active layer.

The gate electrode may have a structure in which a current pathway flowing from a source electrode to a drain electrode can be formed and the amount of current flowing through the current pathway can be controlled by voltage applied to the gate electrode, and the gate electrode is, for example, a comb-type electrode.

FIG. 1 is a schematic cross-sectional view showing one example of the organic transistor of the present invention (electric field-effect type organic transistor). The organic transistor 100 shown in FIG. 1 has a substrate 1, a source electrode 5 and a drain electrode 6 formed at a prescribed interval on the substrate 1, an active layer 2 formed on the substrate 1 so as to cover the source electrode 5 and the drain electrode 6, an insulation layer 3 formed on the active layer 2, and a gate electrode 4 formed on the insulation layer 3 so as to cover the insulation layer 3 on a region between the source electrode 5 and the drain electrode 6.

Figure 2:
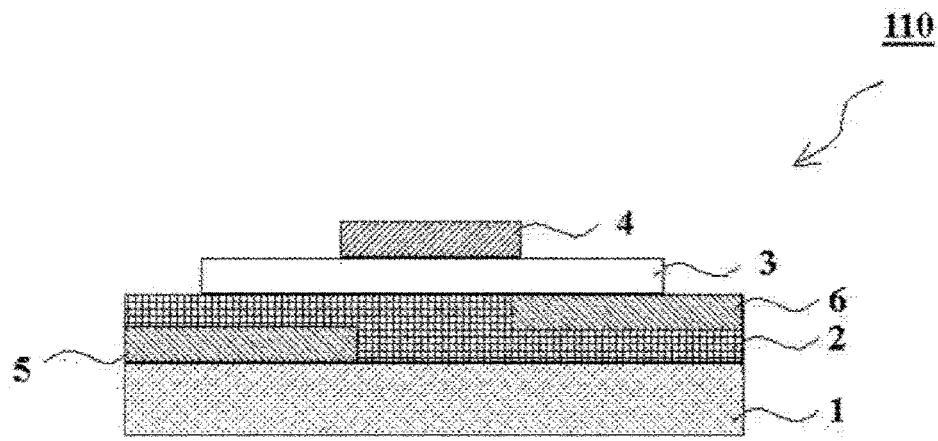
FIG. 2 is a schematic cross-sectional view showing another example of the organic transistor of the present invention.

FIG. 2 is a schematic cross-sectional view showing another example of the organic transistor of the present invention (electric field-effect type organic transistor). The organic transistor 110 shown in FIG. 2 has a substrate 1, a source electrode 5 formed on the substrate 1, an active layer 2 formed on the substrate 1 so as to cover the source electrode 5, a drain electrode 6 formed on the active layer 2 at a prescribed interval from the source electrode 5, an insulation layer 3 formed on the active layer 2 and the drain electrode 6, and a gate electrode 4 formed on the insulation layer 3 so as to cover the insulation layer 3 on a region between the source electrode 5 and the drain electrode 6.

Figure 3:
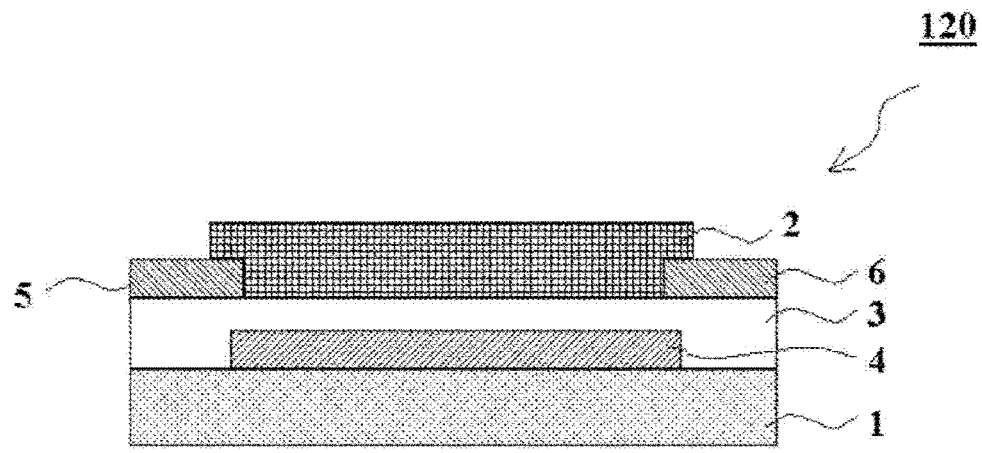
FIG. 3 is a schematic cross-sectional view showing another example of the organic transistor of the present invention.

FIG. 3 is a schematic cross-sectional view showing another example of the organic transistor of the present invention (electric field-effect type organic transistor). The organic transistor 120 shown in FIG. 3 has a substrate 1, a gate electrode 4 formed on the substrate 1, an insulation layer 3 formed on the substrate 1 so as to cover the gate electrode 4, a source electrode 5 and a drain electrode 6 formed at a prescribed interval on the insulation layer 3 so as to cover a part of a region of the insulation layer 3 where the gate electrode 4 is formed below, and an active layer 2 formed on the insulation layer 3 so as to cover a part of the source electrode 5 and the drain electrode 6.

Figure 4:
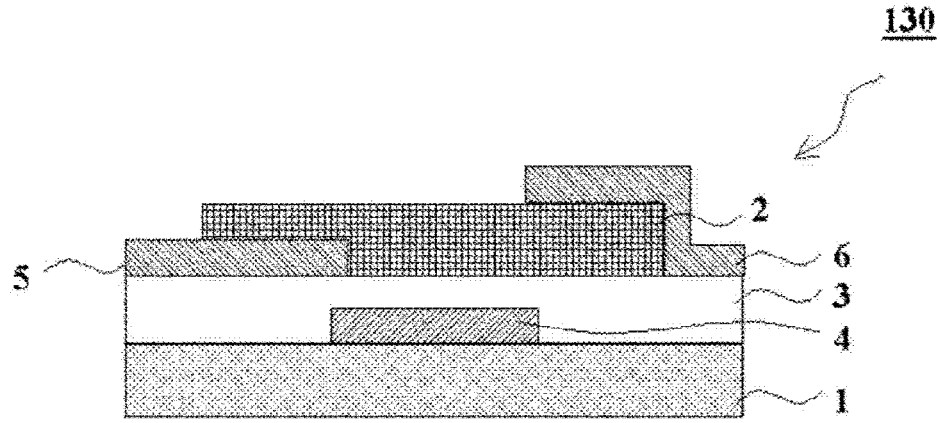
FIG. 4 is a schematic cross-sectional view showing another example of the organic transistor of the present invention.

FIG. 4 is a schematic cross-sectional view showing another example of the organic transistor of the present invention (electric field-effect type organic transistor). The organic transistor 130 shown in FIG. 4 has a substrate 1, a gate electrode 4 formed on the substrate 1, an insulation layer 3 formed on the substrate 1 so as to cover the gate electrode 4, a source electrode 5 formed on the insulation layer 3 so as to cover a part of a region of the insulation layer 3 where the gate electrode 4 is formed below, an active layer 2 formed on the insulation layer 3 so as to cover a part of the source electrode 5, and a drain electrode 6 formed on the insulation layer 3 at a prescribed interval from the source electrode 5 so as to cover a part of the active layer 2.

Figure 5:
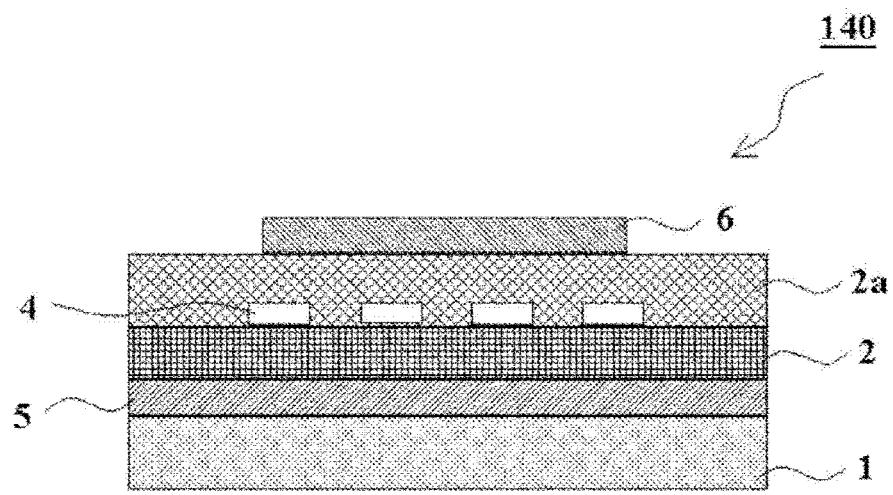
FIG. 5 is a schematic cross-sectional view showing another example of the organic transistor of the present invention.

FIG. 5 is a schematic cross-sectional view showing another example of the organic transistor of the present invention (electric field-effect type organic transistor). The organic transistor 140 shown in FIG. 5 has a substrate 1, a source electrode 5 formed on the substrate 1, an active layer 2 formed on the source electrode 5, several gate electrodes 4 formed at a prescribed interval on the active layer 2, an active layer 2a (the material constituting the active layer 2a may be the same as or different from that of the active layer 2) formed on the active layer 2 so as to cover all the gate electrodes 4, and a drain electrode 6 formed on the active layer 2a.

Figure 6:
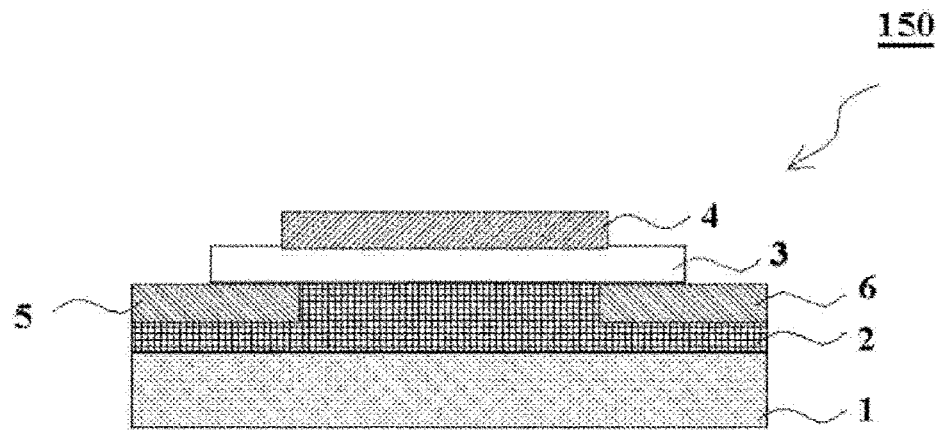
FIG. 6 is a schematic cross-sectional view showing another example of the organic transistor of the present invention.

FIG. 6 is a schematic cross-sectional view showing another example of the organic transistor of the present invention (electric field-effect type organic transistor). The organic transistor 150 shown in FIG. 6 has a substrate 1, an active layer 2 formed on the substrate 1, a source electrode 5 and a drain electrode 6 formed at a prescribed interval on the active layer 2, an insulation layer 3 formed on the active layer 2 so as to cover a part of the source electrode 5 and the drain electrode 6, and a gate electrode 4 formed on the insulation layer 3 so as to cover a part of a region of the insulation layer 3 where the source electrode 5 is formed below and a part of a region of the insulation layer 3 wherein the drain electrode 6 is formed below.

Figure 7:
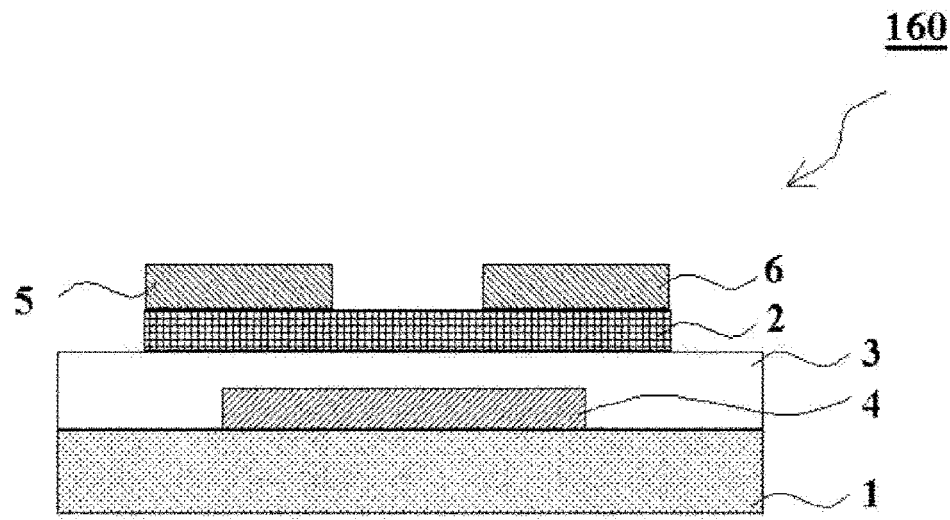
FIG. 7 is a schematic cross-sectional view showing another example of the organic transistor of the present invention.

FIG. 7 is a schematic cross-sectional view showing another example of the organic transistor of the present invention (electric field-effect type organic transistor). The organic transistor 160 shown in FIG. 7 has a substrate 1, a gate electrode 4 formed on the substrate 1, an insulation layer 3 formed on the substrate 1 so as to cover the gate electrode 4, an active layer 2 formed so as to cover a region of the insulation layer 3 where the gate electrode 4 is formed below, a source electrode 5 formed on the active layer 2 so as to cover a part of the active layer 2, and a drain electrode 6 formed on the active layer 2 at a prescribed interval from the source electrode 5 so as to cover a part of the active layer 2.

Figure 8:
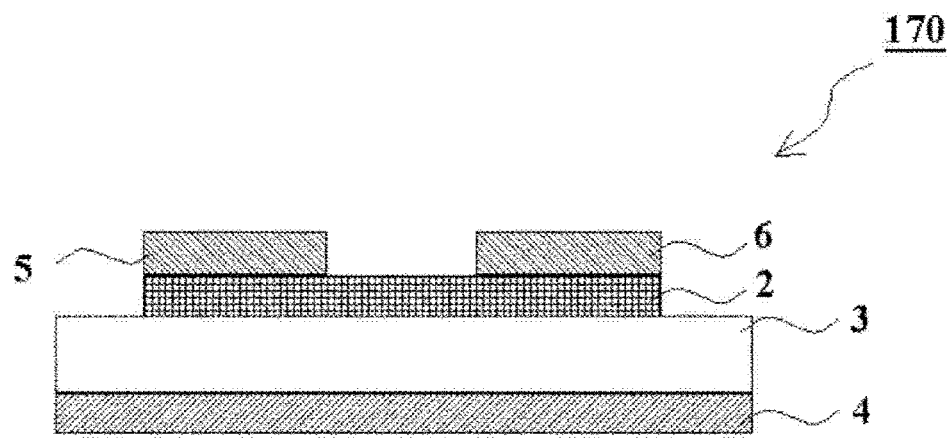
FIG. 8 is a schematic cross-sectional view showing another example of the organic transistor of the present invention.

FIG. 8 is a schematic cross-sectional view showing another example of the organic transistor of the present invention (electric field-effect type organic transistor). The organic transistor 170 shown in FIG. 8 has a gate electrode 4, an insulation layer 3 formed on the gate electrode 4, an active layer 2 formed on the insulation layer 3, and a source electrode 5 and a drain electrode 6 formed at a prescribed interval on the active layer 2. This case has a constitution in which the gate electrode 4 functions also as the substrate 1.

Figure 9:
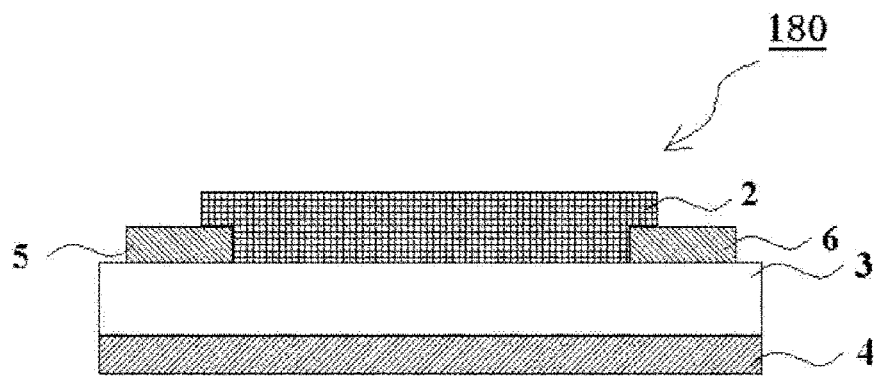
FIG. 9 is a schematic cross-sectional view showing another example of the organic transistor of the present invention.

FIG. 9 is a schematic cross-sectional view showing another example of the organic transistor of the present invention (electric field-effect type organic transistor). The organic transistor 180 shown in FIG. 9 has a gate electrode 4, an insulation layer 3 formed on the gate electrode 4, a source electrode 5 and a drain electrode 6 formed at a prescribed interval on the insulation layer 3, and an active layer 2 formed on the insulation layer 3 so as to cover a part of the source electrode 5 and the drain electrode 6.

In the organic transistor of the present invention described above, the active layer 2 and/or the active layer 2a is constituted of a film containing the compound of the present invention or the polymer compound of the present invention, and functions as a current pathway (channel) between the source electrode 5 and the drain electrode 6. The gate electrode 4 controls the amount of current passing through the current pathway (channel) by applying voltage.

The electric field-effect type organic transistor as described above can be produced by known methods, for example, a method described in JP-A No. 5-110069. In contrast, the electrostatic induction type organic transistor can be produced by known methods such as a method described in JP-A No. 2004-006476, and the like.

The material of the substrate 1 may advantageously be a material not disturbing the property of an organic transistor. As the substrate, a glass substrate, a flexible film substrate and a plastic substrate can be used.

The material of the insulation layer 3 may advantageously be a material showing a high electric insulation property, and $SiO_x$, $SiN_x$, $Ta_2O_5$, polyimide, polyvinyl alcohol, polyvinylphenol, organic glass, photoresist and the like can be used, and from the standpoint of lowering of voltage, a material having a high dielectric constant is preferably used.

When the active layer 2 is formed on the insulation layer 3, it is also possible that the surface of the insulation layer 3 is treated with a surface treatment agent such as a silane coupling agent and the like to attain surface modification, then, the active layer 2 is formed, for improving the interfacial property of the insulation layer 3 and the active layer 2.

In the case of the electric field-effect type transistor, charges such as electrons and holes generally pass around the interface of an insulation layer and an active layer. Therefore, the condition of this interface exerts a significant influence on the electric field-effect mobility of a transistor. Then, as a method of ameliorating the interfacial condition to improve the property, control of the interface with a silane coupling agent is suggested (for example, Surface Chemistry, 2007, vol. 28, no. 5, pp. 242-248).

Examples of the silane coupling agent include alkylchlorosilanes (octyltrichlorosilane (OTS), octadecyltrichlorosilane (ODTS), phenylethyltrichlorosilane and the like), alkylalkoxysilanes, fluorinated alkylchlorosilanes, fluorinated alkylalkoxysilanes, and silylamine compounds such as hexamethyldisilazane (HMDS) and the like. Before treating with a surface treatment agent, the surface of an insulation layer may be treated with ozone and UV or treated with $O_2$ plasma.

By such treatments, the surface energy of a silicon oxidized film and the like used as in insulation layer can be controlled. Further, the orienting property of a film constituting an active layer on in insulation layer is improved and higher electric field-effect mobility is obtained, by the surface treatment.

For the gate electrode 4, metals such as gold, platinum, silver, copper, chromium, palladium, aluminum, indium, molybdenum, low resistance polysilicon, low resistance amorphous silicon and the like, materials such as tin oxide, indium oxide, indium.tin oxide (ITO) and the like can be used.

These materials may be used singly or two or more of them may be used in combination. It is also possible to use a silicon substrate doped at high concentration as the gate electrode 4. The silicon substrate doped at high concentration has a function as a gate electrode and simultaneously also has a function as a substrate. In the case of use of the gate electrode 4 having also such a function as a substrate, the substrate 1 may be omitted in an organic transistor in which the substrate 1 and the gate electrode 4 are adjacent.

The source electrode 5 and the drain electrode 6 are preferably constituted of a material having low resistance, and particularly preferably constituted of gold, platinum, silver, copper, chromium, palladium, aluminum, indium, molybdenum and the like. These materials may be used singly or two or more of them may be used in combination.

In the above-described organic transistor, a layer constituted of other compound may further intervene between the source electrode 5 and drain electrode 6, and the active layer 2. Such a layer includes layers composed of low molecular weight compounds having electron transportability, low molecular weight compounds having hole transportability, alkali metals, alkaline earth metals, rare earth metals, complexes of these metals with organic compounds, halogens such as iodine, bromine, chlorine, iodine chloride and the like, oxidized sulfur compounds such as sulfuric acid, sulfuric anhydride, sulfur dioxide, sulfate and the like, oxidized nitrogen compounds such as nitric acid, nitrogen dioxide, nitrate and the like, halogenated compounds such as perchloric acid, hypochlorous acid and the like, alkylthiol compounds, aromatic thiol compounds such as aromatic thiols, fluorinated alkyl aromatic thiols and the like.

After fabrication of an organic transistor as described above, it is preferable to form a protective film on the organic transistor for protecting the device. By this, the organic transistor is blocked from atmosphere, and lowering of the property of the organic transistor can be suppressed. When a driving display device is formed on an organic transistor, an influence on the organic transistor in its formation process can also be reduced by the protective film.

The method of forming a protective film includes a method of covering an organic transistor with a UV-curing resin, a thermal curing resin, or an inorganic $SiON_x$ film and the like. For performing blocking from atmosphere effectively, it is preferable that after fabrication of an organic transistor, a protective film is formed without exposing the organic transistor to atmosphere (for example, in a dried nitrogen atmosphere, in vacuum, and the like).

An electric field-effect type transistor which is one of organic transistors constituted as described above can be applied as a liquid crystal display of active matrix driving mode, a pixel driving switching device of an organic electroluminescent device, and the like. The electric field-effect type transistor of this embodiment described above contains the compound of the present invention or the polymer compound of the present invention as an active layer, thus has an active layer excellent in mobility, as a result, its electric field-effect mobility is high. Therefore, the electric field-effect type transistor is useful for production of a display having sufficient response speed, and the like.

The present invention can provide a compound and a polymer compound useful for production of an organic transistor excellent in both the electric field-effect mobility and the ON/OFF ratio. Further, the present invention can provide an organic semiconductor material, an organic semiconductor device and an organic transistor containing the compound or the polymer compound.

Further, according to preferable embodiments of the present invention, a compound and a polymer compound having high ionization potential can be provided. By use of the compound and the polymer compound, an organic transistor excellent also in stability of the ON/OFF ratio is expected.

EXAMPLES

Examples are shown below for illustrating the present invention further in detail, but the present invention is not limited to them.

(Mass Spectrometry)
Mass spectrometry was carried out using AccuTOF TLC IMS-T100TD (manufactured by JEOL Ltd.).

(NMR Analysis)
A compound was dissolved in deuterated chloroform, and NMR thereof was measured using an NMR apparatus (manufactured by Varian Medical Systems Inc., INOVA300).

(Molecular Weight Analysis)
The number-average molecular weight and the weight-average molecular weight of a polymer compound were determined using gel permeation chromatography (GPC, manufactured by Waters, trade name: Alliance GPC 2000). The polymer compound to be measured was dissolved in orthodichlorobenzene and injected into GPC.

As the mobile phase of GPC, orthodichlorobenzene was used. As the column, TSKgel GMHHR-H(s)HT (two columns are connected, manufactured by Tosoh Corporation) was used. As the detector, an UV detector was used.

(Analysis of Ionization Potential)
The ionization potential of an organic thin film containing a polymer compound obtained by a method of fabricating an organic transistor described later was determined by measurement using an atmospheric photoelectronic spectrometer (AC-2 manufactured by RIKEN KEIKI Co., Ltd.).

Synthesis Example 1

Synthesis of Compound 2

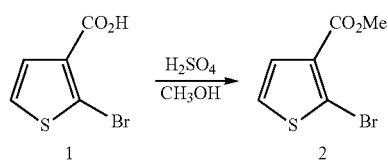

Into a reaction vessel were charged 12.1 g (58.4 mmol) of a compound 1, 10 mL of concentrated sulfuric acid and 250 mL of methanol, and the mixture was refluxed for 6 hours. The resultant reaction solution was poured into water, and extracted with toluene. The resultant toluene solution was concentrated to obtain a liquid which was then purified using a silica gel column, to obtain a compound 2. The gained amount was 12.8 g, and the yield was 99%.

$^1$H-NMR (300 MHz, $CDCl_3$): δ (ppm)=7.36 (d, 1H), 7.22 (d, 1H), 3.88 (s, 3H).

Synthesis Example 2

Synthesis of Compound 4

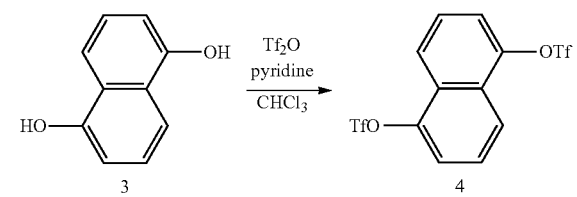

Into a reaction vessel were charged 6.00 g (37.5 mmol) of a compound 3 and 180 mL of pyridine, and the mixture was cooled down to 0° C. Thereafter, into the reaction vessel was added 23.3 g (82.4 mmol) of trifluoroacetic anhydride. The resultant reaction solution was warmed up to room temperature, and 120 mL of chloroform was added and the mixture was stirred for 8 hours. The resultant reaction solution was poured into a sodium hydrogen carbonate aqueous solution, and extracted with chloroform. The resultant chloroform solution was concentrated to obtain a solution which was then poured into methanol, to obtain a deposit. The resultant deposit was isolated by filtration, and washed with methanol, to obtain a compound 4. The gained amount was 10.8 g, and the yield was 68%.

$^1$H-NMR (300 MHz, $CDCl_3$): δ (ppm)=8.14 (d, 2H), 7.70 (t, 2H), 7.61 (d, 2H).

Synthesis Example 3

Synthesis of Compound 5

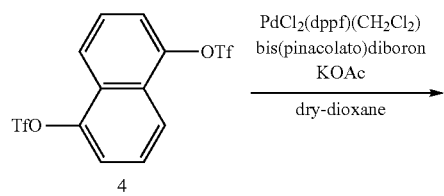

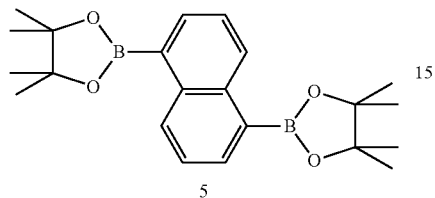

A gas in a reaction vessel was purged with a nitrogen gas, then, 1.00 g (2.36 mmol) of the compound 4, 1.44 g (5.66 mmol) of bispinacolatodiboron, 1.39 g (14.1 mmol) of potassium acetate, 96.2 mg (0.12 mmol) of 1,1'-bis(diphenylphosphino)ferrocene palladium dichloride and 50 mL of dioxane were charged, and refluxed for 8 hours. The resultant reaction solution was filtrated through Celite, and washed with hexane. Thereafter, the resultant solution was poured into water, and extracted with hexane. The resultant hexane solution was concentrated, to obtain a compound 5. The gained amount was 0.88 g, and the yield was 98%.

$^1$H-NMR (300 MHz, CDCl$_3$): δ (ppm)=8.88 (d, 2H), 8.06 (d, 2H), 7.51 (t, 2H), 1.42 (s, 24H).

Synthesis Example 4

Synthesis of Compound 6

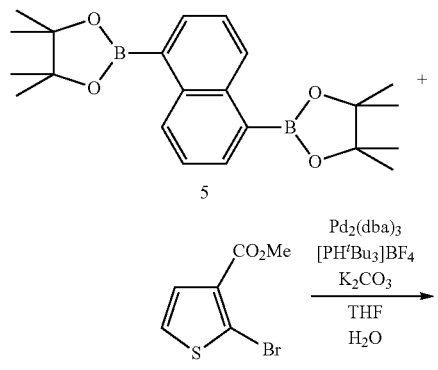

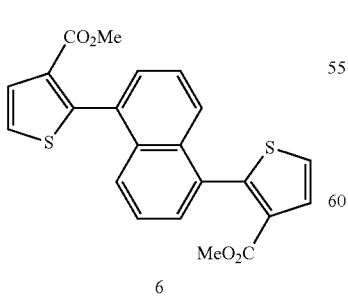

A gas in the reaction vessel was purged with a nitrogen gas, then, 3.40 g (8.95 mmol) of the compound 5, 4.35 g (19.7 mmol) of the compound 2, 0.328 g of tris(dibenzylideneacetone)dipalladium, 0.415 g of tri-tert-butylphosphonium tetrafluoroborate and 100 mL of tetrahydrofuran were charged and stirred. Into the resultant reaction solution, 22 mL of a 2 mol/L potassium carbonate aqueous solution was dropped, and the mixture was refluxed for 5 hours. The resultant reaction solution was poured into water and extracted with toluene. The resultant toluene solution was concentrated, and the resultant solid was purified using a silica gel column, to obtain a compound 6. The gained amount was 3.15 g, and the yield was 86%.

$^1$H-NMR (300 MHz, CDCl$_3$): δ (ppm)=7.69 (d, 2H), 7.64 (d, 2H), 7.35-7.55 (m, 6H), 3.51 (s, 6H).

Example 1

Synthesis of Compound 7

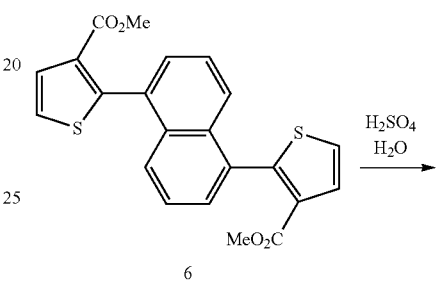

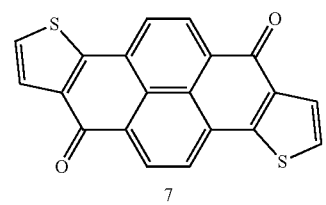

Into a reaction vessel were charged 1.54 g (3.77 mmol) of the compound 6, 54 mL of sulfuric acid and 6 mL of water, and reacted at 130° C. for 5 hours. The resultant reaction solution was poured into water, to obtain a deposit. The resultant deposit was isolated by filtration, and washed with methanol. The resultant solid was purified by sublimation, to obtain a compound 7. The gained amount was 0.31 g, and the yield was 24%.

MS (m/z) 345

Synthesis Example 5

Synthesis of Compound 9

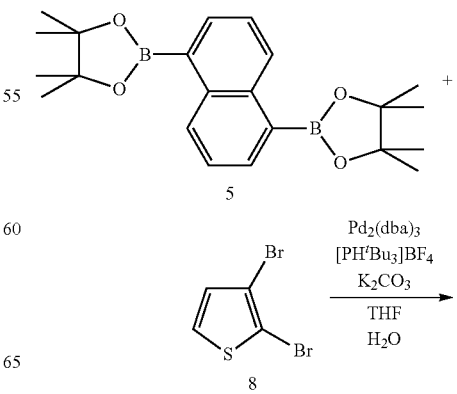

-continued

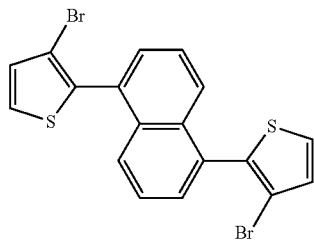

9

A gas in a reaction vessel was purged with a nitrogen gas, then, 7.77 g (20.4 mmol) of the compound 5, 10.9 g (45.0 mmol) of 2,3-dibromothiophene, 0.749 g of tris(dibenzylideneacetone)dipalladium, 0.949 g of tri-tert-butylphosphonium tetrafluoroborate and 100 mL of tetrahydrofuran were charged and stirred. Into the resultant reaction solution, 51 mL of a 2 mol/L potassium carbonate aqueous solution was dropped, and the mixture was refluxed for 5 hours. The resultant reaction solution was poured into water, and extracted with toluene. The resultant toluene solution was concentrated, and the resultant solid was purified using a silica gel column, to obtain a compound 9. The gained amount was 4.30 g, and the yield was 47%.

$^1$H-NMR (300 MHz, CDCl$_3$): δ (ppm)=7.84 (d, 2H), 7.50-7.60 (m, 4H), 7.44 (d, 2H), 7.15 (d, 2H).

Synthesis Example 6

Synthesis of Compound 10

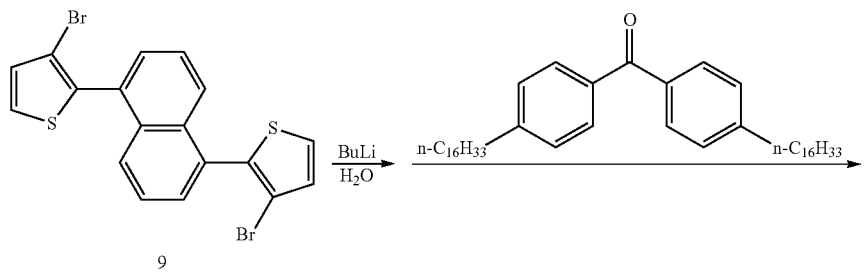

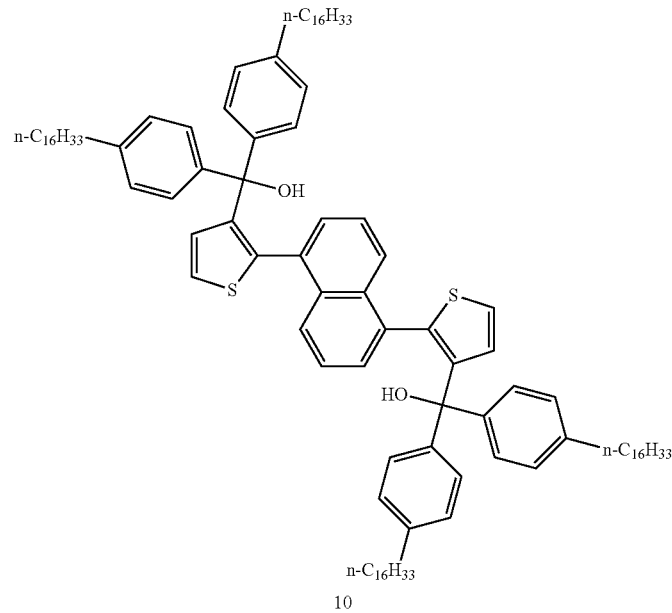

10

Into a reaction vessel were charged 1.00 g (2.22 mmol) of the compound 9 and 300 mL of diethyl ether, and the mixture was cooled down to −78° C. Thereafter, a n-butyllithium hexane solution (1.6 mol/L, 2.92 mL, 4.66 mmol) was dropped into the reaction vessel. The resultant reaction solution was stirred at −78° C. for 1 hour. Thereafter, into the reaction vessel was added 2.94 g (4.66 mmol) of 4,4'-dihexadecylbenzophenone, and the reaction solution was stirred at room temperature for 6 hours. The resultant reaction solution was poured into water, and extracted with diethyl ether. The resultant diethyl ether solution was concentrated, and the resultant solid was purified using a silica gel column, to obtain a compound 10.
The gained amount was 3.05 g, and the yield was 86%.

Example 2

Synthesis of Compound 11

Into a reaction vessel were charged 3.05 g (2.00 mmol) of the compound 10, 0.315 g (2.22 mmol) of a trifluoroborate ether complex and 100 mL of chloroform, and the mixture was stirred for 2 hours. The resultant reaction solution was poured into water, and extracted with chloroform. The resultant chloroform solution was concentrated, and the resultant solid was purified using a silica gel column, to obtain a compound 11. The gained amount was 2.50 g, and the yield was 86%.

$^1$H-NMR (300 MHz, CDCl$_3$): δ (*ppm*)=7.54 (d, 2H), 7.00-7.23 (m, 22H), 6.75 (d, 2H), 2.54 (t, 8H), 1.57 (m, 8H), 1.20-1.40 (m, 104H), 0.88 (t, 12H).

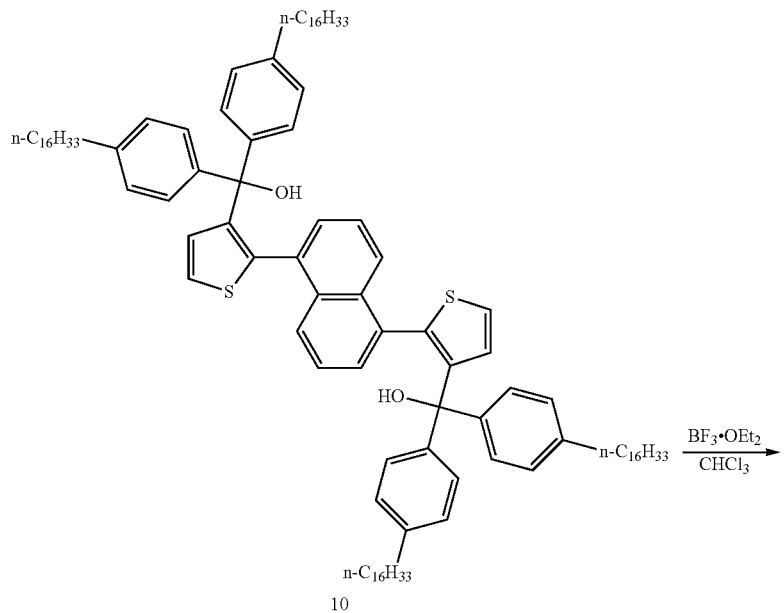

10

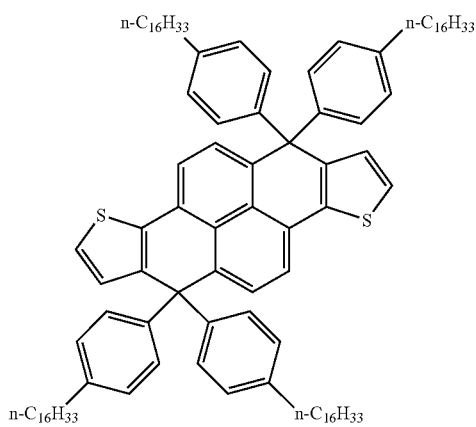

11

Example 3

Synthesis of Compound 12

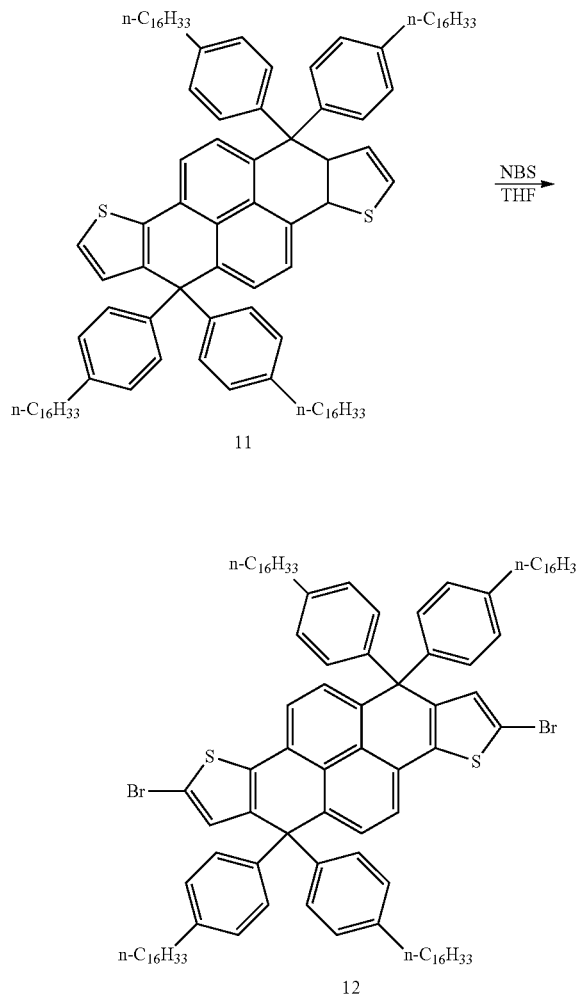

Into a reaction vessel were charged 1.20 g (0.79 mmol) of the compound 5, 0.309 g (1.74 mmol) of N-bromosuccinimide and 50 mL of tetrahydrofuran, and the mixture was refluxed for 4 hours. The resultant reaction solution was poured into water, and extracted with hexane. The resultant hexane solution was washed with water. The resultant hexane solution was concentrated to obtain a liquid which was then purified using a silica gel column, to obtain a compound 6. The gained amount was 0.76 g, and the yield was 57%.

$^1$H-NMR (300 MHz, CDCl$_3$): δ (ppm)=7.24-7.40 (m, 4H), 7.05 (m, 16H), 6.71 (s, 2H), 2.55 (t, 8H), 1.55 (m, 8H), 1.20-1.40 (m, 104H), 0.88 (t, 12H).

Example 4

Synthesis of Polymer Compound A

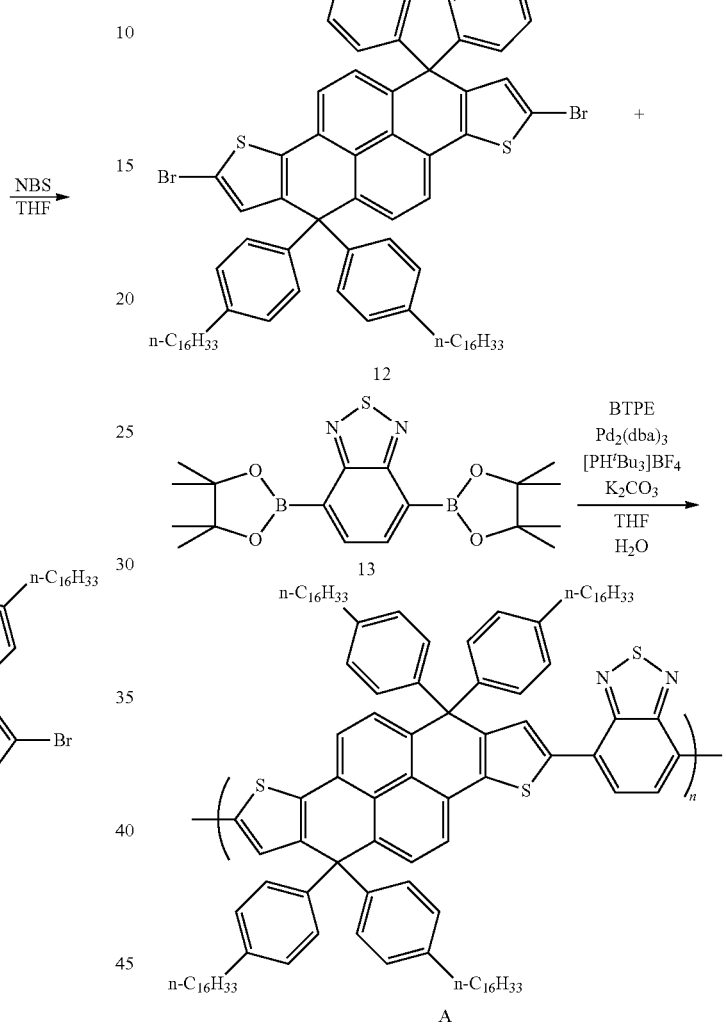

A gas in a reaction vessel was purged with a nitrogen gas, then, 0.200 g (0.119 mmol) of a compound 12, 46.3 mg (0.119 mmol) of a compound 13, 30 mL of tetrahydrofuran, 4.4 mg of tris(dibenzylideneacetone)dipalladium and 5.5 mg of tri-tert-butylphosphonium tetrafluoroborate were charged and stirred. Into the resultant solution, 0.60 mL of a 2 mol/L potassium carbonate aqueous solution was dropped, and the mixture was refluxed for 3 hours.

To the resultant reaction solution was added 10.0 mg of phenylboronic acid, and the mixture was refluxed for 1 hour. To the resultant reaction solution was added 0.1 g of sodium N,N-diethyldithiocarbamate trihydrate, and the mixture was refluxed for 3 hours. The resultant reaction solution was poured into water, toluene was added, and the toluene layer was extracted. The resultant toluene solution was washed with an acetic acid aqueous solution and water, then, purified using a silica gel column. Into the resultant toluene solution, acetone was dropped, obtain a deposit.

The resultant deposit was washed with Soxhlet using acetone as a solvent, to obtain a polymer compound A. The gained amount was 22 mg, and the polystyrene-equivalent number-average molecular weight was $1.5 \times 10^4$ and the polystyrene-equivalent weight-average molecular weight was $3.2 \times 10^4$.

Example 5

Synthesis of Polymer Compound B

A gas in a reaction vessel was purged with a nitrogen gas, then, 0.150 g (0.0895 mmol) of the compound 12, 0.0560 g (0.0895 mmol) of a compound 14, 50 mL of toluene, 1.2 mg of tris(dibenzylideneacetone)dipalladium and 2.5 mg of tri-orthotolylphosphine were charged and refluxed for 5 hours. To the resultant reaction solution was added 30 mg of bromobenzene, and the mixture was refluxed for 1 hour. The resultant reaction solution was dropped into acetone, to obtain a deposit. The resultant deposit was isolated by filtration, and toluene, water and sodium N,N-diethyldithiocarbamate trihydrate were added, and the mixture was refluxed for 3 hours. Thereafter, the toluene layer was extracted. The resultant toluene solution was washed with an acetic acid aqueous solution and water, then, purified using a silica gel column. The resultant toluene solution was dropped into acetone, to obtain a deposit.

The resultant deposit was washed with Soxhlet using acetone as a solvent, to obtain a polymer compound B. The gained amount was 15 mg, and the polystyrene-equivalent number-average molecular weight was $5.0 \times 10^4$ and the polystyrene-equivalent weight-average molecular weight was $1.3 \times 10^5$.

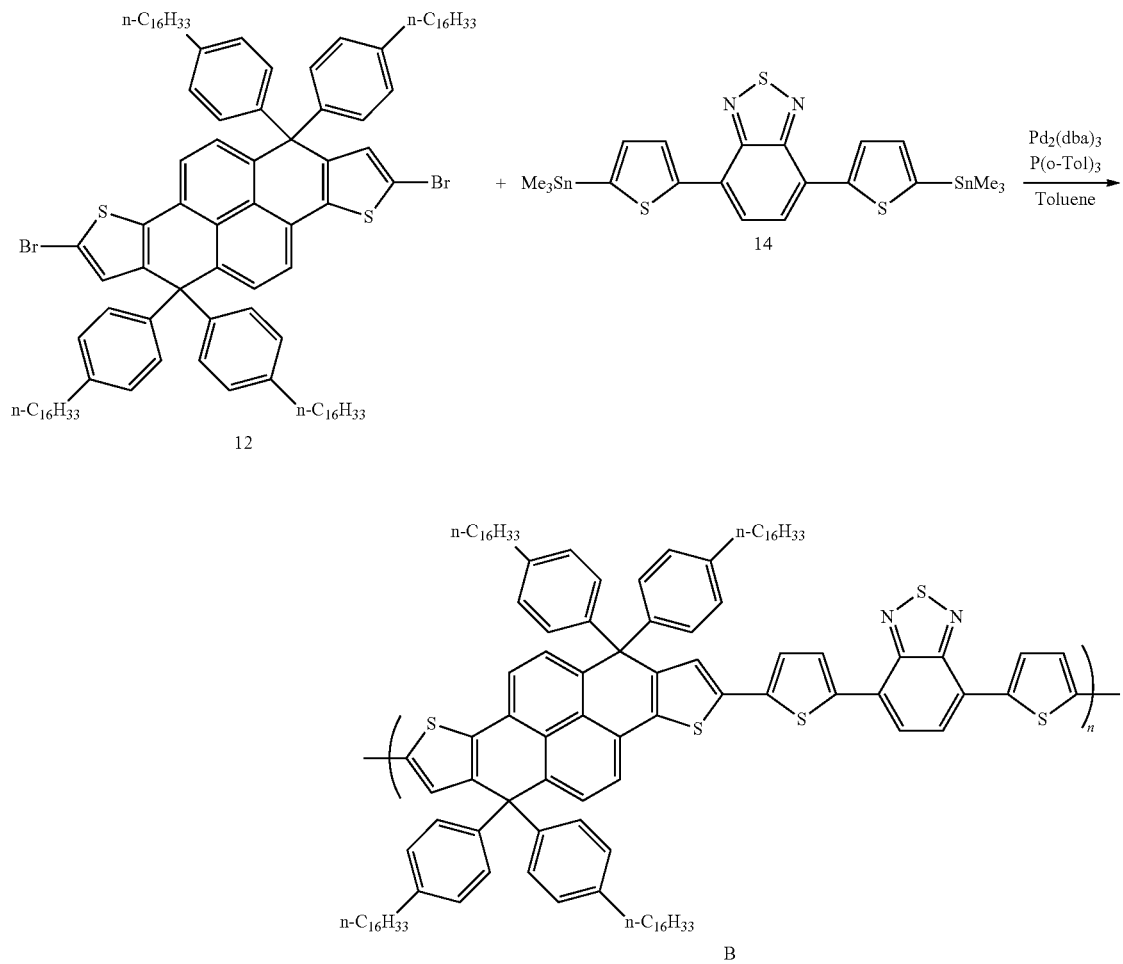

Example 6

Fabrication and Evaluation of Organic Transistor 1

An organic transistor 1 having a structure shown in FIG. 9 was fabricated using a solution containing the polymer compound A.

The surface of an n-type silicon substrate doped at high concentration functioning as a gate electrode was thermally oxidized, to form a silicon oxidized film (hereinafter, referred to as "thermally oxidized film"). The thermally oxidized film functions as an insulation layer. Next, a source electrode and a drain electrode were fabricated on the thermally oxidized film by a photolithography step. The source electrode and the drain electrode had a chromium (Cr) layer and a gold (Au) layer from the thermally oxidized film side, and had a channel length of 20 μm and a channel width of 2 mm. The substrate on which the thermally oxidized film, the source electrode and the drain electrode had been thus formed was washed with ultrasonic wave in acetone, and subjected to a UV ozone treatment using an ozone UV cleaner. Thereafter, the surface of the thermally oxidized film was modified with β-phenethyltrichlorosilane, and the surface of the source electrode and the drain electrode was modified with pentafluorobenzenethiol. Next, on the thermally oxidized film, the source electrode and the drain electrode having undergone the surface treatment, a 0.5 wt % orthodichlorobenzene solution of the polymer compound A was spin-coated at a rotation speed of 1000 rpm, to form an organic semiconductor layer (active layer). Thereafter, the organic semiconductor layer was heated in atmosphere at 170° C. for 30 minutes, to produce an organic transistor 1.

The gate voltage Vg and the source-drain voltage Vsd of the resultant organic transistor 1 were varied, and the transistor properties were measured. The electric field-effect mobility was $1.8 \times 10^{-2}$ cm²/Vs and the ON/OFF ratio was $10^6$. The ionization potential of the organic thin film containing the polymer compound A was 5.5 eV.

Example 7

Fabrication and Evaluation of Organic Transistor 2

An organic transistor 2 was fabricated in the same manner as in Example 6 excepting that the polymer compound B was used instead of the polymer compound A.

The gate voltage Vg and the source-drain voltage Vsd of the resultant organic transistor 2 were varied, and the transistor properties were measured. The electric field-effect mobility was $4.3 \times 10^{-2}$ cm²/Vs and the ON/OFF ratio was $10^6$. The ionization potential of the organic thin film containing the polymer compound B was 5.5 eV.

Example 8

Synthesis of Polymer Compound C

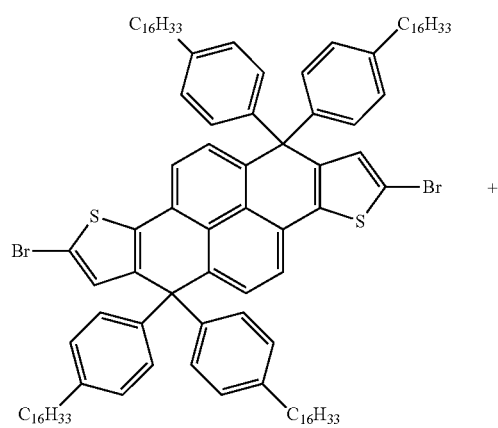

12

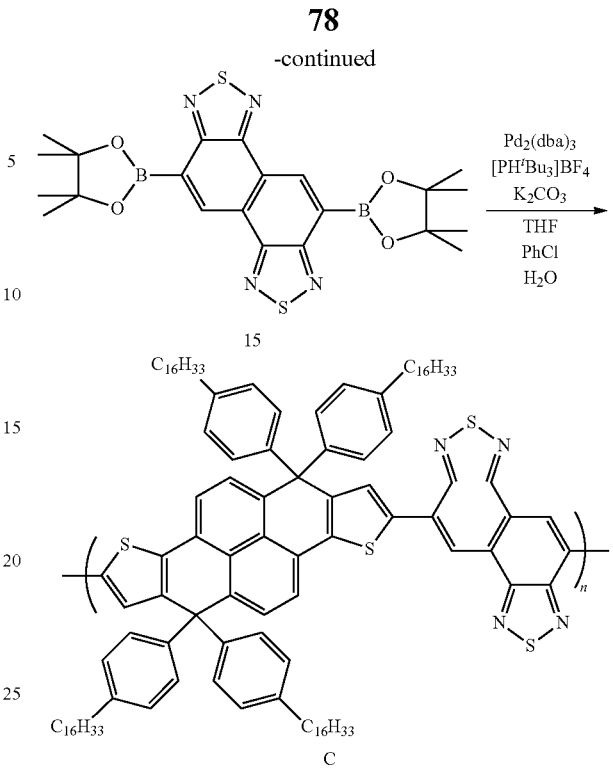

C

A gas in a reaction vessel was purged with a nitrogen gas, then, 0.200 g (0.119 mmol) of the compound 12, 59.2 mg (0.119 mmol) of a compound 15, 30 mL of tetrahydrofuran, 30 mL of chlorobenzene, 4.4 mg of tris(dibenzylideneacetone)dipalladium and 5.5 mg of tri-tert-butylphosphonium tetrafluoroborate were charged and stirred. Into the resultant solution, 0.60 mL of a 2 mol/L potassium carbonate aqueous solution was dropped, and the mixture was refluxed for 3 hours.

To the resultant reaction solution was added 10.0 mg of phenylboronic acid, and the mixture was refluxed for 1 hour. To the resultant reaction solution was added 0.1 g of sodium N,N-diethyldithiocarbamate trihydrate, and the mixture was refluxed for 3 hours. The resultant reaction solution was poured into water, toluene was added, and the toluene layer was extracted. The resultant toluene solution was washed with an acetic acid aqueous solution and water, then, purified using a silica gel column. The resultant toluene solution was dropped into acetone, to obtain a deposit.

The resultant deposit was washed with Soxhlet using acetone as a solvent, to obtain a polymer compound A. The gained amount was 120 mg, and the polystyrene-equivalent number-average molecular weight was $1.6 \times 10^4$ and the polystyrene-equivalent weight-average molecular weight was $3.7 \times 10^4$.

EXPLANTATION OF REFERENCES

1 substrate
2, 2a active layer
3 insulation layer
4 gate electrode
5 source electrode
6 drain electrode
100, 110, 120, 130, 140, 150, 160, 170, 180 organic transistor

The invention claimed is:
1. A polymer compound comprising a structural unit represented by the formula (3):

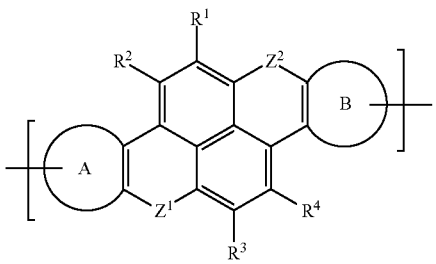
(3)

wherein R¹, R², R³ and R⁴ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by —B(OH)₂) or an organotin residue, and these groups may have a substituent;

the ring A and the ring B represent each independently a heterocyclic ring, and the aromatic ring may have a substituent;

$Z^1$ and $Z^2$ represent each independently one group selected from the group consisting of groups represented by the formula (Z-1) to the formula (Z-11);

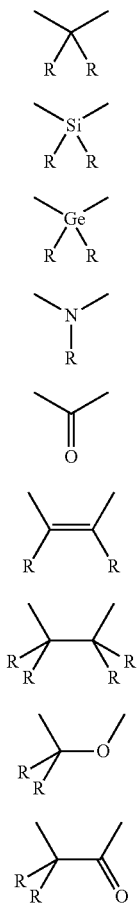

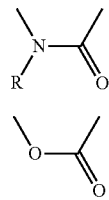
(Z-10)

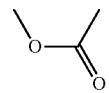
(Z-11)

wherein R represents a hydrogen atom, an alkyl group, an alkoxy group, an alkylthio group, an aryl group, a monovalent heterocyclic group or a halogen atom, and these groups may have a substituent; and when a plurality of R are present, these may be the same or different.

2. The compound according to claim 1, wherein the structural unit represented by the formula (3) is a structural unit represented by the formula (4):

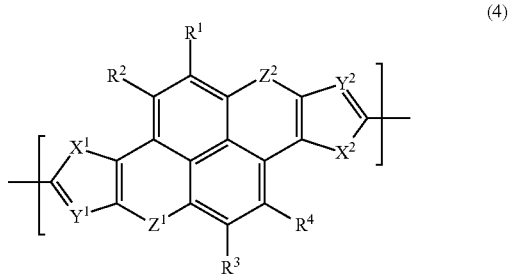
(4)

(wherein wherein R¹, R², R³, R⁴, Z¹ and Z² represent the same meaning as described above;

R⁵ and R⁶ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue (denoting a group represented by —B(OH)₂) or an organotin residue, and these groups may have a substituent;

X¹ and X² represent each independently an oxygen atom, a sulfur atom or a selenium atom;

Y¹ and Y² represent each independently a nitrogen atom or a group represented by —CR⁷═; and R⁷ represents a hydrogen atom, an alkyl group, an alkoxy group, an alkylthio group, an aryl group, a mono-valent heterocyclic group or a halogen atom.

3. The polymer compound according to claim 1, further comprising a structural unit represented by the formula (5):

(5)

wherein Ar represents an arylene group or a di-valent heterocyclic group, and these groups may have a substituent, with the proviso that Ar is different from the structural unit represented by the formula (3).

4. The polymer compound according to claim 3, wherein the structural unit represented by the formula (5) is a structural unit represented by the formula (6):

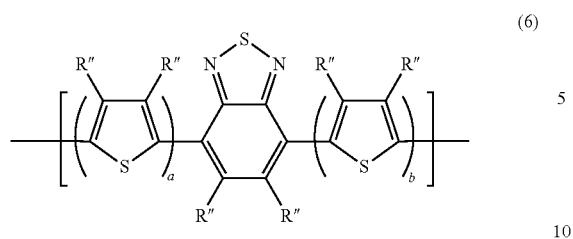 (6)

wherein R" represents a hydrogen atom, an alkyl group, an aryl group, a mono-valent heterocyclic group or a halogen atom; a plurality of R' may be the same or different; and a and b represent each independently an integer of 0 to 5.

5. The polymer compound according to claim 4, wherein the polymer compound is a copolymer of the structural unit represented by the formula (3) and the structural unit represented by the formula (6).

\* \* \* \* \*